United States Patent [19]
Falk et al.

[11] Patent Number: 5,625,124
[45] Date of Patent: Apr. 29, 1997

[54] **ANIMAL MODEL FOR *HELICOBACTER PYLORI* INFECTION**

[75] Inventors: Per Falk, Sollentuna, Sweden; Jeffrey I. Gordon, St. Louis, Mo.

[73] Assignee: Washington University, St. Louis, Mo.

[21] Appl. No.: 273,411

[22] Filed: Jul. 11, 1994

[51] Int. Cl.$^6$ .............................. C12N 5/00; A61K 49/00; G01N 33/567
[52] U.S. Cl. .................. 800/2; 800/DIG. 1; 424/9.2; 435/7.21; 435/172.3; 435/354; 935/59
[58] Field of Search ...................... 424/9, 9.2; 435/7.21, 435/172.1, 172.3, 240.2; 800/2, DIG. 1; 935/59, 60, 70

[56] References Cited

PUBLICATIONS

Keller et al (1992) FEBS Letters 313:265–269.
Strojek et al (1988) Genetic Engineering: Principles and Methods 10: 238.
Kim et al (1993) Diabetes 42: 1799–1808.
Kollias et al (1993) In Grosveld et al, eds, Transgenic Animals, p. 84.
Chandrashekar et al (1994) Mol Androl 6: 95–102.
Loudon et al (1993) Clin Exp Pharmacol Physiol 20: 283–288.
RH Whitehead et al (1993) Proc Natl Acad Sci USA 90:587–591.
GT Merlino (1991) FASEB J: 5:2996–3001.
Baracchini, et al., "Patterns of Intestinal Metaplasia in Gastric Biopsies. A Comparison of Different Histochemical Classifications", *Histochem. J.*, 23:1–9 (1991).
Bird, J.M., et al., "Oligosaccharides Containing Fucose Linked α(1–3) and α(1–4) to N–Acetylglucosamine Cause Decompaction of Mouse Morulae", *Dev. Biol.*, 104:449–460 (1984).
Blaser, M.J., "*Helicobacter Pylori:* Microbiology of a 'Slow' Bacterial Infection", *Trends Microbiol.*, 1:255–260 (Oct. 1993).

Borén, T., et al., "Attachment of *Helicobacter Pylori* to Human Gastric Epithelium Mediated by Blood Group Antigens", *Science* 262:1892–1895 (Dec., 1993).
Clausen, H., et al., "ABH and Related Histo–Blood Group Antigens; Immunochemical Differences in Carrier Isotypes and Their Distribution", *Vox Sang.*, 56:1–20 (1989).
Evans, D.G. et al., "Cloning, Nucleotide Sequence, and Expression of a Gene Encoding an Adhesin Subunit Protein of *Helicobacter Pylori*", *J. Bacteriol.*, 175:674–683 (Feb., 1993).
Falk, P., et al., "Lectins Are Sensitive Tools for Defining the Differentiation Programs of Mouse Gut Epithelial Cell Lineages", *Am. J. Physiol.* (Gastroenterol. Liver Physiol., 266), G987–G1003, (1994).
Falk, P., et al., "An In Vitro Adherence Assay Reveals that *Helicobacter Pylori* Exhibits Cell Lineage–Specific Tropism in the Human Gastric Epithelium", *Proc. Natl. Acad. Sci USA*, 90:2035–2039 (Mar., 1993).
Forman, D., et al., "An International Association Between *Helicobacter Pylori* Infection and Gastric Cancer", (The Eurogast Study Group), *Lancet*, 341:1359–1362 (May, 1993).

(List continued on next page.)

*Primary Examiner*—Bruce R. Campell
*Attorney, Agent, or Firm*—Arnall Golden & Gregory

[57] ABSTRACT

Transgenic non-human animals are described which serve as a model for *H. pylori* infection of epithelial cells of the stomach and small intestine. The gut epithelial cells of the transgenic animals express one or more surface carbohydrate antigens which act as receptors for the bacterium *H. pylori*, a known causative agent of acid peptic disease, such as gastritis, stomach ulcers, duodenal ulcers, and strongly correlated with the development of gastric neoplasia. Methods for making and using the transgenic animals are also disclosed. The transgenic animals can be used to screen for compounds and conditions which block binding of *H. pylori* to the gut epithelium and/or ameliorate the *H. pylori*-associated pathogenesis of acid peptic disease and gastric adenocarcinoma.

9 Claims, 6 Drawing Sheets

PUBLICATIONS

Gossler, A., et al., "Transgenesis by Means of Blastocyst–Derived Embryonic Stem Cell Lines", *Proc. Natl. Acad. Sci. USA*, 83:9065–9069 (Dec., 1986).

Graham, D.Y., et al., "Effect of Treatment of *Helicobacter Pylori* Infection on the Long–Term Recurrence of Gastric or Duodenal Ulcer", *Ann. Int. Med.* 116(9):705–708 (May, 1992).

Granholm, T., et al., "Cytokine Responsiveness in Germfree and Conventional NMRI Mice", *Cytokine*, 4(6):545–550 (Nov., 1992).

Hermiston, M.L., et al., "Chimeric–Transgenic Mice Represent a Powerful Tool for Studying How the Proliferation and Differentiation Programs of Intestinal Epithelial Cell Lineages are Regulated", *Proc. Natl. Acad. Sci. USA*, 90:8866–8870 (Oct. 1993).

Hogan, B., et al., "Microinjection of DNA Into Pronuclei", *In*, Manipulating the mouse embryo, 157–173 (Cold Spring Harbor Laboratory, Cold Spring Harbor, NY, 1986).

Jat, P.S., et al., "Cell Lines Established by a Temperature–Sensitive Simian Virus 40 Large–T–Antigen Gene Are Growth Restricted at the Nonpermissive Temperature", *Mol. Cell Biol.*, 9(4):1672–1681 (Apr., 1989).

Karlsson, K–A., "Animal Glycosphingolipids as Membrane Attachment Sites for Bacteria", *Ann. Rev. Biochem.*, 58:309–350 (1989).

Khillan, J.S., et al., "Gene Transactivation Mediated by the TAT Gene of Human Immunodeficiency Virus Transgenic Mice", *Nucleic Acids Res.*, 16(4):1423–1430 (1988).

Kim, S.H., et al., "Transgenic Mouse Models That Explore the Multistep Hypothesis of Intestinal Neoplasia", *J. Cell Biol.*, 123(4):877–893 (Nov., 1993).

Kukowska–Latallo, J.F., et al., "A Cloned Human cDNA Determines Expression of a Mouse Stage–Specific Embryonic Antigen and the lewis Blood Group $\alpha(1,3/1,4)$Fucosyltransferase", *Genes Dev.*, 4:1288–1303 (1988).

Levine, T., et al., "The Precancer–Cancer Sequence", *In Helicobacter pylori infection* (Northfield, Mendall, and Goggin eds.), 88–89 (Kluwer Acad. Publ., Boston (1993).

Larsen, R.D., et al., "Molecular Cloning, Sequence, and Expression of a Human GDP–L–Fucose:–$\beta$–D–Galactoside 2$\beta$–L–Fucosyltransferase cDNA That Can Form the H Blood Group Antigen", *Proc. Natl. Acad. Sci. USA*, 87:6674–6678 (Sep., 1990).

Madan, E., et al., "Evaluation of Staining Methods for Identifying *Campylobacter Pylori*", *Am. J. Clin. Pathol.*, 90:450–453 (Apr., 1988).

Paulson, J.C., et al., "Glycosyltranferases—Structure, Localization, and Control of Cell Type–Specific Glycosylation", *J. Biol. Chem.*, 264(30):17615–17618 (Oct., 1989).

Roth, K.A., et al., "Regulation of Gene Expression in Gastric Epithelial Cell Populations of Fetal, Neonatal, and Adult Transgenic Mice", *Am. J. Physiol.* (Gastrointest. Liver Physiol., 26), 263–G186–G197 (1992).

Rubin, D.C., et al., "Use of Fetal Intestinal Isografts from Normal and Transgenic Mice to Study the Programming of Positional Information Along the Duodenal–to–Colonic Axis", *J. Biol. Chem.*, 267(21):15122–15133 (Jul., 1992).

Rubin, D.C., et al., "Use of Isografts to Study Proliferation and Differentiation Programs of Mouse Stomach Epithelia", *Am. J. Physiol.* (Gastroenterol. Liver Physiol., 30), 267:G27–G39, (1994).

Sakamoto, J., et al., "Expression of Lewis$^a$, Lewis$^b$, Lewis$^x$, Lewis$^y$, Sialyl–Lewis$^a$, and Sialyl–Lewis$^x$ Blood Group Antigens in Human Gastric Carcinoma and in Normal Gastric Tissue", *Cancer Res.*, 49:745–752 (Feb., 1989).

Sanchez, J., et al., "Binding of Bacteria to Carbohydrates Immobilized on Beads to Demonstrate the Presence of Cell–Associated Hemagglutinins in *Vibrio Chlorae*", *Acta Pathol. Microbiol. Immunol. Scand.*, 98:353–357 (1990).

Sandgren, E.P., et al., "Overexpression of TGF$\alpha$ in Transgenic Mice: Induction of Epithelial Hyperplasia, Pancreatic Metaplasia, and Carcinoma of the breast", *Cell*, 61:1121–1135 (Jun., 1990).

Sharon, N., et al., "Lectins as Cell Recognition Molecules", *Science*, 246:227–234 (1989).

Simon, T.C., et al., "Use of Transgenic Mice to Map *cis*–Acting Elements in the Liver Fatty Acid–Binding Protein Gene (Fabpl) That Regulate Its Cell Lineage–Specific, Differentiation–Dependent, and Spatial Patterns of Expression in the Gut Epithelium and in the Liver Acinus", *J. Biol. Chem.*, 268(24):18345–18358 (1993).

Tosh, F.D., "Characterization of a Fucoside–Binding Adhesin of *Candida Albicans*", *Infect. Immun.*, 60(11):4734–4739 (Nov., 1992).

Trahair, J.E., et al., "Use of Transgenic Mice to Study the Routing of Secretory Proteins in Intestinal Epithelial Cells: Analysis of Human Growth Hormone Compartmentalization as a Function of Cell Type and Differentiation", *J. Cell Biol.*, 109:3231–3242 (Dec., 1989).

"Transient Expression of Proteins Using COS Cells", *In Current Protocols in Molecular Biology*, 2:16.13.1–16.13.7, Ausubel, F.M., et al., eds. (John Wiley & Sons, New York, 1991) by Dr. Jan Holgersson (Department of Molecular Biology, Massachusetts General Hospital, Boston, Massachusetts).

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 365 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( i x ) FEATURE:
        ( A ) NAME/KEY: misc_feature
        ( B ) LOCATION: 1..365
        ( D ) OTHER INFORMATION: /note=
            " GDP-L- fucose:beta-D-Galactoside-2-alpha-L-fucosyl ( x ) PUBLICATION INFORMATION:
        ( A ) AUTHORS: Larsen, et al.
        ( C ) JOURNAL: Proc. Nat'l Acad. Sci. USA
        ( D ) VOLUME: 87
        ( F ) PAGES: 6674-6678
        ( G ) DATE: 1990
        ( K ) RELEVANT RESIDUES IN SEQ ID NO:1: FROM 1 TO 365

( x i ) SEQUENCE DESCRIPTION: SEQ ID NO:1:

```
Met  Trp  Leu  Arg  Ser  His  Arg  Gln  Leu  Cys  Leu  Ala  Phe  Leu  Leu  Val
 1              5                        10                       15

Cys  Val  Leu  Ser  Val  Ile  Phe  Phe  Leu  His  Ile  His  Gln  Asp  Ser  Phe
              20                        25                       30

Pro  His  Gly  Leu  Gly  Leu  Ser  Ile  Leu  Cys  Pro  Asp  Arg  Arg  Leu  Val
              35                        40                       45
```

| | | | | | | | | | | | | | | |
|---|---|---|---|---|---|---|---|---|---|---|---|---|---|---|
| Thr | Pro | Pro | Val | Ala | Ile | Phe | Cys | Leu | Pro | Gly | Thr | Ala | Met | Gly | Pro |
| | 50 | | | | 55 | | | | | 60 | | | | |
| Asn | Ala | Ser | Ser | Ser | Cys | Pro | Gln | His | Pro | Ala | Ser | Leu | Ser | Gly | Thr |
| 65 | | | | 70 | | | | | 75 | | | | | 80 |
| Trp | Thr | Val | Tyr | Pro | Asn | Gly | Arg | Phe | Gly | Asn | Gln | Met | Gly | Gln | Tyr |
| | | | | 85 | | | | | 90 | | | | | 95 | |
| Ala | Thr | Leu | Leu | Ala | Leu | Ala | Gln | Leu | Asn | Gly | Arg | Arg | Ala | Phe | Ile |
| | | | 100 | | | | | 105 | | | | | 110 | | |
| Leu | Pro | Ala | Met | His | Ala | Ala | Leu | Ala | Pro | Val | Phe | Arg | Ile | Thr | Leu |
| | | 115 | | | | | 120 | | | | | 125 | | | |
| Pro | Val | Leu | Ala | Pro | Glu | Val | Asp | Ser | Arg | Thr | Pro | Trp | Arg | Glu | Leu |
| | 130 | | | | 135 | | | | | 140 | | | | | |
| Gln | Leu | His | Asp | Trp | Met | Ser | Glu | Glu | Tyr | Ala | Asp | Leu | Arg | Asp | Pro |
| 145 | | | | | 150 | | | | 155 | | | | | | 160 |
| Phe | Leu | Lys | Leu | Ser | Gly | Phe | Pro | Cys | Ser | Trp | Thr | Phe | Phe | His | His |
| | | | | 165 | | | | | 170 | | | | | 175 | |
| Leu | Arg | Glu | Gln | Ile | Arg | Arg | Glu | Phe | Thr | Leu | His | Asp | His | Leu | Arg |
| | | | 180 | | | | | 185 | | | | | 190 | | |
| Glu | Glu | Ala | Gln | Ser | Val | Leu | Gly | Gln | Leu | Arg | Leu | Gly | Arg | Thr | Gly |
| | | 195 | | | | | 200 | | | | | 205 | | | |
| Asp | Arg | Pro | Arg | Thr | Phe | Val | Gly | Val | His | Val | Arg | Arg | Gly | Asp | Tyr |
| | 210 | | | | | 215 | | | | | 220 | | | | |
| Leu | Gln | Val | Met | Pro | Gln | Arg | Trp | Lys | Gly | Val | Val | Gly | Asp | Ser | Ala |
| 225 | | | | | 230 | | | | 235 | | | | | | 240 |
| Tyr | Leu | Arg | Gln | Ala | Met | Asp | Trp | Phe | Arg | Ala | Arg | His | Glu | Ala | Pro |
| | | | | 245 | | | | | 250 | | | | | 255 | |
| Val | Phe | Val | Val | Thr | Ser | Asn | Gly | Met | Glu | Trp | Cys | Lys | Glu | Asn | Ile |
| | | | 260 | | | | | 265 | | | | | 270 | | |
| Asp | Thr | Ser | Gln | Gly | Asp | Val | Thr | Phe | Ala | Gly | Asp | Gly | Gln | Glu | Ala |
| | | 275 | | | | | 280 | | | | | 285 | | | |
| Thr | Pro | Trp | Lys | Asp | Phe | Ala | Leu | Leu | Thr | Gln | Cys | Asn | His | Thr | Ile |
| | 290 | | | | | 295 | | | | | 300 | | | | |
| Met | Thr | Ile | Gly | Thr | Phe | Gly | Phe | Trp | Ala | Ala | Tyr | Leu | Ala | Gly | Gly |
| 305 | | | | | 310 | | | | 315 | | | | | | 320 |
| Asp | Thr | Val | Tyr | Leu | Ala | Asn | Phe | Thr | Leu | Pro | Asp | Ser | Glu | Phe | Leu |
| | | | | 325 | | | | | 330 | | | | | 335 | |
| Lys | Ile | Phe | Lys | Pro | Glu | Ala | Ala | Phe | Leu | Pro | Glu | Trp | Val | Gly | Ile |
| | | | 340 | | | | | 345 | | | | | 350 | | |
| Asn | Ala | Asp | Leu | Ser | Pro | Leu | Trp | Thr | Leu | Ala | Lys | Pro | | | |
| | | 355 | | | | | 360 | | | | | 365 | | | |

( 2 ) INFORMATION FOR SEQ ID NO:2:

( i ) SEQUENCE CHARACTERISTICS:
        ( A ) LENGTH: 3373 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 104..1201
        ( D ) OTHER INFORMATION: /note="Nucleotides 104 through 1201
            encode the GDP-L- fuc ( x ) PUBLICATION INFORMATION:
    ( A ) AUTHORS: Larsen, et al.
    ( C ) JOURNAL: Proc. Nat'l Acad. Sci. USA
    ( D ) VOLUME: 87
    ( F ) PAGES: 6674-6678
    ( G ) DATE: 1990
    ( K ) RELEVANT RESIDUES IN SEQ ID NO:2: FROM 1 TO 3373

( x i ) SEQUENCE DESCRIPTION: SEQ ID NO:2:

```
GCCTGGCGTT  CCAGGGGCGG  CCGGATGTGG  CCTGCCTTTG  CGGAGGGTGC  GCTCCGGCCA      60
CGAAAAGCGG  ACTGTGGATC  TGCCACCTGC  AAGCAGCTCG  GCCATGTGGC  TCCGGAGCCA     120
TCGTCAGCTC  TGCCTGGCCT  TCCTGCTAGT  CTGTGTCCTC  TCTGTAATCT  TCTTCCTCCA     180
TATCCATCAA  GACAGCTTTC  CACATGGCCT  AGGCCTGTCG  ATCCTGTGTC  AGACCGCCG      240
CCTGGTGACA  CCCCCAGTGG  CCATCTTCTG  CCTGCCGGGT  ACTGCGATGG  GCCCCAACGC     300
CTCCTCTTCC  TGTCCCCAGC  ACCCTGCTTC  CCTCCGGC    ACCTGGACTG  TCTACCCCAA     360
TGGCCGGTTT  GGTAATCAGA  TGGGACAGTA  TGCCACGCTG  CTGGCTCTGG  CCCAGCTCAA     420
CGGCCGCCGG  GCCTTTATCC  TGCCTGCCAT  GCATGCCGCC  CTGGCCCCGG  TATTCCGCAT     480
CACCCTGCCC  GTGCTGGCCC  CAGAAGTGGA  CAGCCGCACG  CCGTGGCGGG  AGCTGCAGCT     540
TCACGACTGG  ATGTCGGAGG  AGTACGCGGA  CTTGAGAGAT  CCTTTCCTGA  AGCTCTCTGG     600
CTTCCCCTGC  TCTTGGACTT  TCTTCCACCA  TCTCCGGGAA  CAGATCCGCA  GAGAGTTCAC     660
CCTGCACGAC  CACCTTCGGG  AAGAGGCGCA  GAGTGTGCTG  GGTCAGCTCC  GCCTGGGCCG     720
CACAGGGGAC  CGCCCGCGCA  CCTTTGTCGG  CGTCCACGTG  CGCCGTGGGG  ACTATCTGCA     780
GGTTATGCCT  CAGCGCTGGA  AGGGTGTGGT  GGGCGACAGC  GCCTACCTCC  GGCAGGCCAT     840
GGACTGGTTC  CGGGCACGGC  ACGAAGCCCC  CGTTTTCGTG  GTCACCAGCA  ACGGCATGGA     900
GTGGTGTAAA  GAAAACATCG  ACACCTCCCA  GGGCGATGTG  ACGTTTGCTG  GCGATGGACA     960
GGAGGCTACA  CCGTGGAAAG  ACTTTGCCCT  GCTCACACAG  TGCAACCACA  CCATTATGAC    1020
CATTGGCACC  TTCGGCTTCT  GGGCTGCCTA  CCTGGCTGGC  GGAGACACTG  TCTACCTGGC    1080
CAACTTCACC  CTGCCAGACT  CTGAGTTCCT  GAAGATCTTT  AAGCCGGAGG  CGGCCTTCCT    1140
GCCCGAGTGG  GTGGGCATTA  ATGCAGACTT  GTCTCCACTC  TGGACATTGG  CTAAGCCTTG    1200
AGAGCCAGGG  AGACTTTCTG  AAGTAGCCTG  ATCTTTCTAG  AGCCAGCAGT  ACGTGGCTTC    1260
AGAGGCCTGG  CATCTTCTGG  AGAAGCTTGT  GGTGTTCCTG  AAGCAAATGG  GTGCCCGTAT    1320
CCAGAGTGAT  TCTAGTTGGG  AGAGTTGGAG  AGAAGGGGGA  CGTTTCTGGA  ACTGTCTGAA    1380
TATTCTAGAA  CTAGCAAAAC  ATCTTTTCCT  GATGGCTGGC  AGGCAGTTCT  AGAAGCCACA    1440
GTGCCCACCT  GCTCTTCCCA  GCCCATATCT  ACAGTACTTC  CAGATGGCTG  CCCCCAGGAA    1500
TGGGGAACTC  TCCCTCTGGT  CTACTCTAGA  AGAGGGGTTA  CTTCTCCCCT  GGGTCCTCCA    1560
AAGACTGAAG  GAGCATATGA  TTGCTCCAGA  GCAAGCATTC  ACCAAGTCCC  CTTCTGTGTT    1620
TCTGGAGTGA  TTCTAGAGGG  AGACTTGTTC  TAGAGAGGAC  CAGGTTTGAT  GCCTGTGAAG    1680
AACCCTGCAG  GGCCCTTATG  GACAGGATGG  GGTTCTGGAA  ATCCAGATAA  CTAAGGTGAA    1740
GAATCTTTTT  AGTTTTTTTT  TTTTTTTTT   GGAGACAGGG  TCTCGCTCTG  TTGCCCAGGC    1800
TGGAGTGCAG  TGGCGTGATC  TTGGCTCACT  GCAACTTCCG  CCTCCTGTGT  TCAAGCGATT    1860
CTCCTGTCTC  AGCCTCCTGA  GTAGATGGGA  CTACAGGCAC  AGGCCATTAT  GCCTGGCTAA    1920
TTTTTGTATT  TTTAGTAGAG  ACAGGGTTTC  ACCATGTTGG  CCGGGATGGT  CTCGATCTCC    1980
TGACCTTGTC  ATCCACCTGT  CTTGGCCTCC  CAAAGTGCTG  GGATTACTGG  CATGAGCCAC    2040
TGTGCCCAGC  CCGGATATTT  TTTTTAATT   ATTATTTAT   TTATTTATTT  ATTGAGACGG    2100
```

| | | | | | | |
|---|---|---|---|---|---|---|
| AGTCTTGCTC | TGTAGCCCAG | GCCAGAGTGC | AGTGGCGCGA | TCTCAGCTCA | CTGCAAGCTC | 2160 |
| TGCCTCCCGG | GTTCATGCCA | TTCTGCCTCA | GCCTCCTGAG | TAGCTGGGAC | TACAGGCGCC | 2220 |
| CGCCACCACG | CCCGGCTAAT | TTTTTTTGTA | TTTTAGTAG | AGACGGGGTT | TCATCGTGTT | 2280 |
| AACCAGGATG | GTCTCGATCT | CCTGACCTCG | TGATCTGCCC | ACCTCGGCCT | CCCACAGTGC | 2340 |
| TGGGATTACC | GGCGTGAGCC | ACCATGCCTG | GCCCGGATAA | TTTTTTTTAA | TTTTGTAGA | 2400 |
| GACGAGGTCT | TGTGATATTG | CCCAGGCTGT | TCTTCAACTC | CTGGGCTCAA | GCAGTCCTCC | 2460 |
| CACCTTGGCC | TCCCAGAATG | CTGGGTTTAT | AGATGTGAGC | CAGCACACCG | GCCAAGTGA | 2520 |
| AGAATCTAAT | GAATGTGCAA | CCTAATTGTA | GCATCTAATG | AATGTTCCAC | CATTGCTGGA | 2580 |
| AAAATTGAGA | TGGAAAACAA | ACCATCTCTA | GTTGGCCAGC | GTCTTGCTCT | GTTCACAGTC | 2640 |
| TCTGGAAAAG | CTGGGGTAGT | TGGTGAGCAG | AGCGGGACTC | TGTCCAACAA | GCCCCACAGC | 2700 |
| CCCTCAAAGA | CTTTTTTTG | TTTGTTTGA | GCAGACAGGC | TAAAATGTGA | ACGTGGGGTG | 2760 |
| AGGGATCACT | GCCAAAATGG | TACAGCTTCT | GGAGCAGAAC | TTTCCAGGGA | TCCAGGGACA | 2820 |
| CTTTTTTTA | AAGCTCATAA | ACTGCCAAGA | GCTCCATATA | TTGGGTGTGA | GTTCAGGTTG | 2880 |
| CCTCTCACAA | TGAAGGAAGT | TGGTCTTTGT | CTGCAGGTGG | GCTGCTGAGG | GTCTGGGATC | 2940 |
| TGTTTCTGG | AAGTGTGCAG | GTATAAACAC | ACCCTCTGTG | CTTGTGACAA | ACTGGCAGGT | 3000 |
| ACCGTGCTCA | TTGCTAACCA | CTGTCTGTCC | CTGAACTCCC | AGAACCACTA | CATCTGGCTT | 3060 |
| TGGGCAGGTC | TGAGATAAAA | CGATCTAAAG | GTAGGCAGAC | CCTGGACCCA | GCCTCAGATC | 3120 |
| CAGGCAGGAG | CACGAGGTCT | GGCCAAGGTG | GACGGGGTTG | TCGAGATCTC | AGGAGCCCCT | 3180 |
| TGCTGTTTTT | TGGAGGGTGA | AAGAAGAAAC | CTTAAACATA | GTCAGCTCTG | ATCACATCCC | 3240 |
| CTGTCTACTC | ATCCAGACCC | CATGCCTGTA | GGCTTATCAG | GGAGTTACAG | TTACAATTGT | 3300 |
| TACAGTACTG | TTCCCAACTC | AGCTGCCACG | GGTGAGAGAG | CAGGAGGTAT | GAATTAAAAG | 3360 |
| TCTACAGCAC | TAA | | | | | 3373 |

( 2 ) INFORMATION FOR SEQ ID NO:3:

( i ) SEQUENCE CHARACTERISTICS:
        ( A ) LENGTH: 361 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( i x ) FEATURE:
        ( A ) NAME/KEY: misc_feature
        ( B ) LOCATION: 1..361
        ( D ) OTHER INFORMATION: /note=
            " GDP-L- fucose:beta-D-N-acetylglucosaminide-3,4-alp ( x ) PUBLICATION INFORMATION:
        ( A ) AUTHORS: Kukowska-Latallo, et al.
        ( C ) JOURNAL: Genes & Development
        ( D ) VOLUME: 4
        ( F ) PAGES: 1288-1303
        ( G ) DATE: 1990
        ( K ) RELEVANT RESIDUES IN SEQ ID NO:3: FROM 1 TO 361

( x i ) SEQUENCE DESCRIPTION: SEQ ID NO:3:

```
Met  Asp  Pro  Leu  Gly  Ala  Ala  Lys  Pro  Gln  Trp  Pro  Trp  Arg  Arg  Cys
 1              5                        10                           15
```

```
Leu Ala Ala Leu Leu Phe Gln Leu Leu Val Ala Val Cys Phe Phe Ser
            20                  25                  30

Tyr Leu Arg Val Ser Arg Asp Asp Ala Thr Gly Ser Pro Arg Ala Pro
        35                  40                  45

Ser Gly Ser Ser Arg Gln Asp Thr Thr Pro Thr Arg Pro Thr Leu Leu
    50                  55                  60

Ile Leu Leu Trp Thr Trp Pro Phe His Ile Pro Val Ala Leu Ser Arg
65                  70                  75                  80

Cys Ser Glu Met Val Pro Gly Thr Ala Asp Cys His Ile Thr Ala Asp
                85                  90                  95

Arg Lys Val Tyr Pro Gln Ala Asp Thr Val Ile Val His His Trp Asp
            100                 105                 110

Ile Met Ser Asn Pro Lys Ser Arg Leu Pro Pro Ser Pro Arg Pro Gln
        115                 120                 125

Gly Gln Arg Trp Ile Trp Phe Asn Leu Glu Pro Pro Pro Asn Cys Gln
    130                 135                 140

His Leu Glu Ala Leu Asp Arg Tyr Phe Asn Leu Thr Met Ser Tyr Arg
145                 150                 155                 160

Ser Asp Ser Asp Ile Phe Thr Pro Tyr Gly Trp Leu Glu Pro Trp Ser
                165                 170                 175

Gly Gln Pro Ala His Pro Pro Leu Asn Leu Ser Ala Lys Thr Glu Leu
            180                 185                 190

Val Ala Trp Ala Val Ser Asn Trp Lys Pro Asp Ser Ala Arg Val Arg
        195                 200                 205

Tyr Tyr Gln Ser Leu Gln Ala His Leu Lys Val Asp Val Tyr Gly Arg
    210                 215                 220

Ser His Lys Pro Leu Pro Lys Gly Thr Met Met Glu Thr Leu Ser Arg
225                 230                 235                 240

Tyr Lys Phe Tyr Leu Ala Phe Glu Asn Ser Leu His Pro Asp Tyr Ile
                245                 250                 255

Thr Glu Lys Leu Trp Arg Asn Ala Leu Glu Ala Trp Ala Val Pro Val
            260                 265                 270

Val Leu Gly Pro Ser Arg Ser Asn Tyr Glu Arg Phe Leu Pro Pro Asp
        275                 280                 285

Ala Phe Ile His Val Asp Asp Phe Gln Ser Pro Lys Asp Leu Ala Arg
    290                 295                 300

Tyr Leu Gln Glu Leu Asp Lys Asp His Ala Arg Tyr Leu Ser Tyr Phe
305                 310                 315                 320

Arg Trp Arg Glu Thr Leu Arg Pro Arg Ser Phe Ser Trp Ala Leu Asp
                325                 330                 335

Phe Cys Lys Ala Cys Trp Lys Leu Gln Gln Glu Ser Arg Tyr Gln Thr
            340                 345                 350

Val Arg Ser Ile Ala Ala Trp Phe Thr
        355                 360
```

( 2 ) INFORMATION FOR SEQ ID NO:4:

( i ) SEQUENCE CHARACTERISTICS:
        ( A ) LENGTH: 2043 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: misc_feature
  ( B ) LOCATION: 1..361
  ( D ) OTHER INFORMATION: /note="Nucleotides 73 through 1158 encode the GDP-L- fuco ( x ) PUBLICATION INFORMATION:
  ( A ) AUTHORS: Kukowska-Latallo, et al.
  ( C ) JOURNAL: Genes & Development
  ( D ) VOLUME: 4
  ( F ) PAGES: 1288-1303
  ( G ) DATE: 1990
  ( K ) RELEVANT RESIDUES IN SEQ ID NO:4: FROM 1 TO 2043

( x i ) SEQUENCE DESCRIPTION: SEQ ID NO:4:

| | | | | | | |
|---|---|---|---|---|---|---|
| AGGAAACCTG | CCATGGCCTC | CTGGTGAGCT | GTCCTCATCC | ACTGCTCGCT | GCCTCTCCAG | 60 |
| ATACTCTGAC | CCATGGATCC | CCTGGGTGCA | GCCAAGCCAC | AATGGCCATG | GCGCCGCTGT | 120 |
| CTGGCCGCAC | TGCTATTTCA | GCTGCTGGTG | GCTGTGTGTT | TCTTCTCCTA | CCTGCGTGTG | 180 |
| TCCCGAGACG | ATGCCACTGG | ATCCCCTAGG | GCTCCCAGTG | GGTCCTCCCG | ACAGGACACC | 240 |
| ACTCCCACCC | GCCCCACCCT | CCTGATCCTG | CTATGGACAT | GGCCTTTCCA | CATCCCTGTG | 300 |
| GCTCTGTCCC | GCTGTTCAGA | GATGGTGCCC | GGCACAGCCG | ACTGCCACAT | CACTGCCGAC | 360 |
| CGCAAGGTGT | ACCCACAGGC | AGACACGGTC | ATCGTGCACC | ACTGGGATAT | CATGTCCAAC | 420 |
| CCTAAGTCAC | GCCTCCCACC | TTCCCCGAGG | CCGCAGGGGC | AGCGCTGGAT | CTGGTTCAAC | 480 |
| TTGGAGCCAC | CCCCTAACTG | CCAGCACCTG | GAAGCCCTGG | ACAGATACTT | CAATCTCACC | 540 |
| ATGTCCTACC | GCAGCGACTC | CGACATCTTC | ACGCCCTACG | GCTGGCTGGA | GCCGTGGTCC | 600 |
| GGCCAGCCTG | CCCACCCACC | GCTCAACCTC | TCGGCCAAGA | CCGAGCTGGT | GGCCTGGGCG | 660 |
| GTGTCCAACT | GGAAGCCGGA | CTCAGCCAGG | GTGCGCTACT | ACCAGAGCCT | GCAGGCTCAT | 720 |
| CTCAAGGTGG | ACGTGTACGG | ACGCTCCCAC | AAGCCCCTGC | CAAGGGGAC | CATGATGGAG | 780 |
| ACGCTGTCCC | GGTACAAGTT | CTACCTGGCC | TTCGAGAACT | CCTTGCACCC | CGACTACATC | 840 |
| ACCGAGAAGC | TGTGGAGGAA | CGCCCTGGAG | GCCTGGGCCG | TGCCCGTGGT | GCTGGGCCCC | 900 |
| AGCAGAAGCA | ACTACGAGAG | GTTCCTGCCA | CCCGACGCCT | TCATCCACGT | GGACGACTTC | 960 |
| CAGAGCCCCA | AGGACCTGGC | CCGGTACCTG | CAGGAGCTGG | ACAAGGACCA | CGCCCGCTAC | 1020 |
| CTGAGCTACT | TTCGCTGGCG | GGAGACGCTG | CGGCCTCGCT | CCTTCAGCTG | GGCACTGGAT | 1080 |
| TTCTGCAAGG | CCTGCTGGAA | ACTGCAGCAG | GAATCCAGGT | ACCAGACGGT | GCGCAGCATA | 1140 |
| GCGGCTTGGT | TCACCTGAGA | GGCCGGCATG | GTGCCTGGGC | TGCCGGGAAC | CTCATCTGCC | 1200 |
| TGGGGCCTCA | CCTGCTGGAG | TCCTTTGTGG | CCAACCCTCT | CTCTTACCTG | GACCTCACA | 1260 |
| CGCTGGGCTT | CACGGCTGCC | AGGAGCCTCT | CCCCTCCAGA | AGACTTGCCT | GCTAGGGACC | 1320 |
| TCGCCTGCTG | GGGACCTCGC | CTGTTGGGGA | CCTCACCTGC | TGGGGACCTC | ACCTGCTGGG | 1380 |
| GACCTTGGCT | GCTGGAGGCT | GCACCTACTG | AGGATGTCGG | CGGTCGGGGA | CTTTACCTGC | 1440 |
| TGGGACCTGC | TCCCAGAGAC | CTTGCCACAC | TGAATCTCAC | CTGCTGGGGA | CCTCACCCTG | 1500 |
| GAGGGCCCTG | GGCCCTGGGG | AACTGGCTTA | CTTGGGGCCC | CACCCGGGAG | TGATGGTTCT | 1560 |
| GGCTGATTTG | TTTGTGATGT | TGTTAGCCGC | CTGTGAGGGG | TGCAGAGAGA | TCATCACGGC | 1620 |
| ACGGTTTCCA | GATGTAATAC | TGCAAGGAAA | AATGATGACG | TGTCTCCTCA | CTCTAGAGGG | 1680 |
| GTTGGTCCCA | TGGGTTAAGA | GCTCACCCCA | GGTTCTCACC | TCAGGGGTTA | AGAGCTCAGA | 1740 |
| GTTCAGACAG | GTCCAAGTTC | AAGCCCAGGA | CCACCACTTA | TAGGGTACAG | GTGGGATCGA | 1800 |
| CTGTAAATGA | GGACTTCTGG | AACATTCCAA | ATATTCTGGG | GTTGAGGGAA | ATTGCTGCTG | 1860 |

| | | | | | |
|---|---|---|---|---|---|
| TCTACAAAAT | GCCAAGGGTG | GACAGGCGCT | GTGGCTCACG | CCTGTAATTC | CAGCACTTTG | 1920 |
| GGAGGCTGAG | GTAGGAGGAT | TGATTGAGGC | CAAGAGTTAA | AGACCAGCCT | GGTCAATATA | 1980 |
| GCAAGACCAC | GTCTCTAAAT | AAAAATAAT | AGGCCGGCCA | GGAAAAAAA | AAAAAAAAA | 2040 |
| AAA | | | | | | 2043 |

( 2 ) INFORMATION FOR SEQ ID NO:5:

( i ) SEQUENCE CHARACTERISTICS:
        ( A ) LENGTH: 2771 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x ) PUBLICATION INFORMATION:
        ( A ) AUTHORS: Sweetser, et al.
        ( C ) JOURNAL: Genes & Dev.
        ( D ) VOLUME: 2
        ( F ) PAGES: 1318-1332
        ( G ) DATE: 1988
        ( K ) RELEVANT RESIDUES IN SEQ ID NO:5: FROM 561 TO 629

( x ) PUBLICATION INFORMATION:
        ( A ) AUTHORS: Seeburg, et al.
        ( C ) JOURNAL: DNA
        ( D ) VOLUME: 1
        ( F ) PAGES: 239-249
        ( G ) DATE: 1982
        ( K ) RELEVANT RESIDUES IN SEQ ID NO:5: FROM 620 TO 2771

( x ) PUBLICATION INFORMATION:
        ( A ) AUTHORS: Sweetser, et al.
        ( C ) JOURNAL: J. Biol. Chem.
        ( D ) VOLUME: 261
        ( F ) PAGES: 5553-5561
        ( G ) DATE: 1986
        ( K ) RELEVANT RESIDUES IN SEQ ID NO:5: FROM 1 TO 617

( x i ) SEQUENCE DESCRIPTION: SEQ ID NO:5:

| | | | | | |
|---|---|---|---|---|---|
| AATTCTCAGA | ATACAAAACA | GCTTTAGGGA | CTGATAAAAT | ATATGTAAAA | TTATGTTTGT | 60 |
| ATAATAATAG | AAAAATTGAG | AAATAAACAT | AAGGCTACGT | GAAAAGGTTT | TGAGTTCAAA | 120 |
| GGTATTTTTC | TCCACGTAAT | GCACATATAC | ATGTGTGTTT | ATATATGTGC | ATATGTATAT | 180 |
| GTAGCTACAT | GTGTATAAAT | ATATTACATA | TACAAGTGTG | CACATGTATA | AACACATACA | 240 |
| TATGTACACA | TAGGTATATA | TGCATGTATG | CATTGCTAGA | GATGTGATTC | ACATGTCTGT | 300 |
| TGCACATATA | TACATCTGTC | AACATACATT | TCATGTATGC | ACTCTTATTT | CATGAGCGGT | 360 |
| GATAAGACAC | CAAAAATGCA | CCATTTACAG | AGAGCTTTGC | CCTTGATTGG | ACTCACTAAT | 420 |
| GTTTGCTGAA | TTAGAACAAA | CTTCTGCCTT | GCCCATTCTG | ATTTTATCG | TTGACCATTG | 480 |
| CTCTCAGGAG | TTAATGTTTG | ATCCTGGCCA | TAAAGAAATC | GACAATCACT | GACCTATGGC | 540 |
| CTATATTTGA | GGAGGAAGAA | GCCCCTTATA | AAATAGCCAA | CAGTGGGTGG | CCTGGCAGAC | 600 |
| AGAGCTGTTG | TGGTCAGGGG | GATCCCAAGG | CCCAACTCCC | CGAACCACTC | AGGGTCCTGT | 660 |
| GGACAGCTCA | CTAGCGGCAA | TGGCTACAGG | TAAGCGCCCC | TAAATCCCT | TTGGGCACAA | 720 |
| TGTGTCCTGA | GGGGAGAGGC | AGCGACCTGT | AGATGGGACG | GGGGCACTAA | CCCTCAGGTT | 780 |
| TGGGGCTTCT | GAATGAGTAT | CGCCATGTAA | GCCCAGTATG | GCCAATCTCA | GAAAGCTCCT | 840 |
| GGTCCCTGGA | GGGATGGAGA | GAGAAAAACA | AACAGCTCCT | GGAGCAGGGA | GAGTGCTGGC | 900 |
| CTCTTGCTCT | CCGGCTCCCT | CTGTTGCCCT | CTGGTTTCTC | CCCAGGCTCC | CGGACGTCCC | 960 |

```
TGCTCCTGGC TTTTGGCCTG CTCTGCCTGC CCTGGCTTCA AGAGGGCAGT GCCTTCCCAA      1020

CCATTCCCTT ATCCAGGCTT TTTGACAACG CTAGTCTCCG CGCCCATCGT CTGCACCAGC      1080

TGGCCTTTGA CACCTACCAG GAGTTTGTAA GCTCTTGGGG AATGGGTGCG CATCAGGGGT      1140

GGCAGGAAGG GGTGACTTTC CCCCGCTGGG AAATAAGAGG AGGAGACTAA GGAGCTCAGG      1200

GTTTTCCCG AAGCGAAAAT GCAGGCAGAT GAGCACACGC TGAGTGAGGT TCCCAGAAAA       1260

GTAACAATGG GAGCTGGTCT CCAGCGTAGA CCTTGGTGGG CGGTCCTTCT CCTAGGAAGA      1320

AGCCTATATC CCAAAGGAAC AGAAGTATTC ATTCCTGCAG AACCCCAGA CCTCCCTCTG       1380

TTTCTCAGAG TCTATTCCGA CACCCTCCAA CAGGGAGGAA ACACAACAGA AATCCGTGAG      1440

TGGATGCCTT GACCCCAGGC GGGGATGGGG GAGACCTGTA GTCAGAGCCC CCGGGCAGCA      1500

CAGGCCAATG CCCGTCCTTC CCCTGCAGAA CCTAGAGCTG CTCCGCATCT CCCTGCTGCT      1560

CATCCAGTCG TGGCTGGAGC CCGTGCAGTT CCTCAGGAGT GTCTTGCCA ACAGCCTGGT       1620

GTACGGCGCC TCTGACAGCA ACGTCTATGA CCTCCTAAAG GACCTAGAGG AAGGCATCCA      1680

AACGCTGATG GGGGTGGGGG TGGCGCTAGG GGTCCCCAAT CTTGGAGCCC CACTGACTTT      1740

GAGAGCTGTG TTAGAGAAAC ACTGCTGCCC TCTTTTAGC AGTCCAGGCC CTGACCCAAG       1800

AGAACTCACC TTATTCTTCA TTTCCCCTCG TGAATCCTCT AGCCTTTCTC TACACCCTGA      1860

AGGGGAGGGA GGAAAATGAA TGAATGAGAA AGGGAGGGAG CAGTACCCAA GCGCTTGGCC      1920

TCTCCTTCTC TTCCTTCACT TTGCAGAGGC TGGAAGATGG CAGCCCCGG ACTGGGCAGA       1980

TCTTCAAGCA GACCTACAGC AAGTTCGACA CAAACTCACA CAACGATGAC GCACTACTCA      2040

AGAACTACGG GCTGCTCTAC TGCTTCAGGA AGGACATGGA CAAGGTCGAG ACATTCCTGC      2100

GCATCGTGCA GTGCCGCTCT GTGGAGGGCA GCTGTGGCTT CTAGCTGCCC GGGTGGCATC      2160

CCTGTGACCC CTCCCCAGTG CCTCTCCTGG CCTTGGAAGT TGCCACTCCA GTGCCCACCA      2220

GCCTTGTCCT AATAAAATTA AGTTGCATCA TTTTGTCTGA CTAGGTGTCC TCTATAATAT      2280

TATGGGGTGG AGGGGGGTGG TTTGGAGCAA GGGGCCCAAG TTGGGAAGAC AACCTGTAGG      2340

GCCTGCGGGG TCTATTCGGG AACCAAGCTG GAGTGCAGTG GCACAATCTT GGCTCACTGC      2400

AATCTCCGCC TCCTGGGTTC AAGCGATTCT CCTGCCTCAG CCTCCCGAGT TGTTGGGATT      2460

CCAGGCATGC ATGACCAGGC TCAGCTAATT TTTGTTTTTT TGGTAGAGAC GGGGTTTCAC      2520

GATATTGGCC AGGCTGGTCT CCAACTCCTA ATCTCAGGTG ATCTACCCAC CTTGGCCTCC      2580

CAAATTGCTG GGATTACAGG CGTGAACCAC TGCTCCCTTC CCTGTCCTTC TGATTTAAA      2640

ATAACTATAC CAGCAGGAGG ACGTCCAGAC ACAGCATAGG CTACCTGCCA TGCCCAACC      2700

GGTGGGACAT TTGAGTTGCT TGCTTGGCAC TGTCCTCTCA TGCGTTGGGT CCACTCAGTA      2760

GATGCCTGTT G                                                          2771
```

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( i x ) FEATURE:
        ( A ) NAME/KEY: misc_feature (B) LOCATION: 1..24
(D) OTHER INFORMATION: /note="Primer derived from
      nucleotides 1078 through 1101

(xi) SEQUENCE DESCRIPTION: SEQ ID NO:6:

AGCTGGCCTT TGACACCTAC CAGG  24

(2) INFORMATION FOR SEQ ID NO:7:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (synthetic)

(iii) HYPOTHETICAL: NO (iv) ANTI-SENSE: YES (ix) FEATURE:
       (A) NAME/KEY: misc_feature
       (B) LOCATION: 1..24
       (D) OTHER INFORMATION: /note="Primer that is complementary
           to nucleotides 1407

(xi) SEQUENCE DESCRIPTION: SEQ ID NO:7:

TCTGTTGTGT TTCCTCCCTG TTGG  24

(2) INFORMATION FOR SEQ ID NO:8:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (synthetic)

(iii) HYPOTHETICAL: NO (iv) ANTI-SENSE: YES (ix) FEATURE:
       (A) NAME/KEY: misc_feature
       (B) LOCATION: 1..22
       (D) OTHER INFORMATION: /note="Primer that is complementary
           to nucleotides 219 t (xi) SEQUENCE DESCRIPTION: SEQ ID NO:8:

CGGCGGTCTG GACACAGGAT CG  22

(2) INFORMATION FOR SEQ ID NO:9:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (synthetic)

(iii) HYPOTHETICAL: NO (iv) ANTI-SENSE: YES (ix) FEATURE:
       (A) NAME/KEY: misc_feature
       (B) LOCATION: 1..23
       (D) OTHER INFORMATION: /note="Primer that is complementary
           to nucleotides 788 t (xi) SEQUENCE DESCRIPTION: SEQ ID NO:9:

```
GGCCAGGTAG  AACTTGTACC  GGG                                              2 3
```

( 2 ) INFORMATION FOR SEQ ID NO:10:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: DNA (synthetic)

( i i i ) HYPOTHETICAL: NO ( i v ) ANTI-SENSE: NO ( i x ) FEATURE:
        ( A ) NAME/KEY: misc_feature
        ( B ) LOCATION: 1..11
        ( D ) OTHER INFORMATION: /note="HindIII site and Kozac sequence."

( x i ) SEQUENCE DESCRIPTION: SEQ ID NO:10:

```
AGCTTGCCAC  C                                                             1 1
```

ANIMAL MODEL FOR *HELICOBACTER PYLORI* INFECTION

The United States Government has rights in this invention as a result of National Institutes of Health grants DK37960 and DK30292 to Jeffrey I. Gordon.

This application is generally in the field of transgenic animals, and in particular, transgenic animals are described which can serve as an animal model for *Helicobacter pylori* infection.

BACKGROUND OF THE INVENTION

Recently, it has been found that the bacterium *Helicobacter pylori* is a causative agent of human chronic gastritis, gastric and duodenal ulcers, as well as gastric adenocarcinoma in humans. (Blaser, *Trends Microbiol.*, 7: 255–260 (1993)). *H. pylori* produces sialic acid-specific agglutinins enabling the bacterium to bind sialyl residue containing carbohydrates. However, studies using an in vitro adherence assay and other data have revealed that strains of *H. pylori* isolated from patients with acid peptic disease bind preferentially to the surface mucous and pit cells in the human gastric epithelium. This binding does not depend on the presence of sialic acid epitopes, but fucose residues constitute an essential recognition element of the epithelial cell's adhesion receptor (Falk et al., *Proc. Natl. Acad. Sci. USA*, 90: 2035–2039 (1993)). Additional studies have indicated that adherence of clinical isolates of *H. pylori* (P466 and WV229) to human gastric surface mucous cells occurs via the $Le^b$ antigen (Borén, et al., *Science*, 262: 1892–1895 (1993)), a fucosylated carbohydrate expressed by members of the pit cell lineage (Sakamoto, et al., *Cancer Res.*, 49: 745–752 (1989); Falk, et al., *Proc. Natl. Acad. Sci. USA*, 90: 2035–2039 (1993). Solid phase binding and inhibition assays also indicated that the human H-1 blood group antigen, a monofucosylated carbohydrate that biochemically defines the blood group O phenotype, may also serve as a specific receptor for bacterial binding. In addition, such binding appears to be specific for the human gut, because binding to comparable cell lineages in the mouse, rat and dog is either significantly weaker, as in Sprague-Dawley rats, or not detectable, as in FVB/N mice. Thus, *H. pylori* has been found to preferentially bind to distinct molecules, such as the $Le^b$ and H-1 antigens, and to sialic acid residues found on glycoproteins on the surface of gastric epithelial cells (Borén et al., *Science*, 262: 1892–1895 (1993); Evans et al., *J. Bacteriol.*, 175: 674–683 (1993)).

Combined chemotherapy with antibiotics (tetracycline and metronidazole), $H_2$ blockers (ranitidine), and bismuth subsalicylate have been used with some success for treating *H. pylori*-associated ulcers, although relapse remains a clinical problem (Graham, et al., *Ann. Int. Med.*, 116: 705–708 (1991)). The exact mechanism by which this bacterium causes chronic active gastritis, gastric and duodenal ulcers and gastric adenocarcinoma remains unclear. It is well documented that *H. pylori* infection of gut epithelial is strongly correlated with development of gastric adenocarcinoma (six to twelve times increased risk according to Forman, et al., *Lancet*, 341: 1359–1363 (1993)). Gastric adenocarcinoma is the fourth leading cause of cancer death worldwide (Levine and Price, In *Helicobacter pylori infection* (Northfield, Mendall, and Goggin eds.), pp. 88–89 (Kluwer Acad. Publ., Boston (1993)).

An effective alternative to antibiotic therapy that is curative and/or prevents *H. pylori*-associated disease has not been developed. An animal model for *H. pylori* infection of the stomach and/or intestinal tract would thus be highly desirable not only for detailed in vivo studies of *H. pylori*-associated diseases caused by wild type and genetically engineered strains, but also for the systematic development and screening for new antibiotics, non-antibiotic compounds, and various other therapies employing natural products and chemically synthesized compositions of matter which are effective in blocking *H. pylori* adhesion, infection, or the subsequent development of *H. pylori*-associated disease states. In addition, an animal model for *H. pylori* infection in the stomach and intestinal tract could be used in developing and assessing effective gene therapies against *H. pylori*-associated gastritis, ulcers, carcinomas, and presumably other *H. pylori*-associated diseases, as well as examining the efficacy of various methods used to immunize the host so as to prevent or ameliorate *H. pylori* infection.

It is therefore an object of the present invention to provide an animal model for *H. pylori* infection and pathogenesis.

It is a further object of the present invention to provide a method for screening and evaluating compounds which block *H. pylori* adhesion to gut endothelium or ameliorate the effects of *H. pylori* binding on the pathogenesis of acid peptic disease.

SUMMARY OF THE INVENTION

Transgenic non-human animals which stably express nucleic acid molecules encoding the human GDP-L-fucose: β-D-galactoside 2-α-L-fucosyltransferase (EC 2.4.1.69, also referred to as α1,2 fucosyl transferase or β1,2FT) and/or the human GDP-L-fucose: β-D-N-acetylglucosaminide 3/4-α-L-fucosyltransferase (also called α1,3/4 fucosyltransferase or α1,3/4 FT) preferentially exhibit fucosylated epitopes, such as the H-1 and $Le^b$ antigens and related structures, on the surfaces of gut epithelial cells. These animals can serve as an animal model for *H. pylori* adhesion and associated diseases and be used to systematically screen for compounds that block *H. pylori* adhesion, or in other ways to intervene in *H. pylori* infection of the stomach or intestinal tract.

As demonstrated by the example, transgenic mice have been made by constructing a transgene including a gut epithelial cell specific promoter and a nucleotide sequence encoding a human fucosyltransferase (FT).

DETAILED DESCRIPTION OF THE INVENTION

Figure 1:
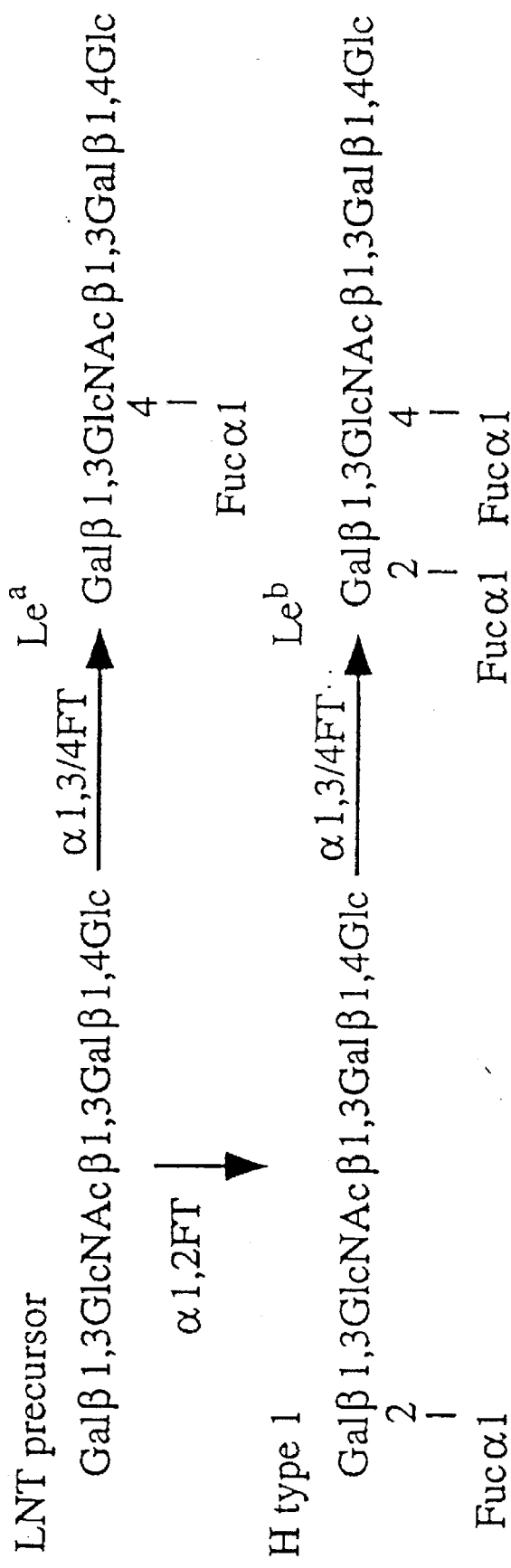
FIG. 1 is a diagram illustrating the formation of the H type 1 blood antigen and the $Le^a$ and $Le^b$ antigens mediated by α1,2 FT and α1,3/4 FT.

*H. pylori* produces adhesins that enable the bacterium to bind human H antigen or Lewis antigens on lacto-series type 1 chains found on the surface of gut epithelial cells. For an animal to serve as an accurate and reliable animal model of *H. pylori* gut infection, it must be capable of producing on the surfaces of gut epithelial cells these antigens which function as receptors for *H. pylori* and, thereby, enable the bacterium to establish an initial attachment and subsequent infection in a manner similar to that in humans. Transgenic animals are described that express the fucosyltransferases (FTs) which enable the gut epithelial cells of the animals to produce one or more of the known *H. pylori* receptor antigens, such as the H type 1 and Le$^b$ antigens, on their cell surfaces. These transgenic animals can therefore serve as an animal model for *H. pylori* infection of the stomach and/or intestinal tract. This animal model is particularly useful to systematically test or screen for compounds which block *H. pylori* adhesion and infection and which are useful in preventing or treating *H. pylori*-associated disease states such as chronic gastritis, ulcers, and gastric adenocarcinoma.

Synthesis of Complex Carbohydrate Receptors

Complex carbohydrates are ubiquitous in the plasma membranes of eukaryotic cells. All complex carbohydrates are composed of highly variable sequences of monosaccharide units (primarily glucose, galactose, N-acetylglucosamine, N-acetylgalactosamine, fucose, sialic acid, and mannose) linked together at different binding positions with different anomerity (α or β) of the glycosidic linkages. Complex carbohydrates can be anchored to a protein via linkage between the innermost N-acetylglucosamine residue of the carbohydrate and asparagine residues in the peptide core (N-linked, the most common in membrane-associated glycoproteins), or via linkage between the innermost N-acetylgalactosamine residue of the carbohydrate to serine or threonine in the peptide core (O-linked or mucin-type). Glycosphingolipids, the glycosides of N-acylsphingosine, are the lipid-bound glycoconjugates of eukaryotic cell membranes. They carry oligosaccharides similar to their glycoprotein counterparts.

The synthesis of complex carbohydrates is mediated by glycosyltransferases, a group of highly specific enzymes (generally associated with the Golgi apparatus) that add activated (nucleotide conjugated) sugars to carbohydrate chains in a step-by-step elongation process. These enzymes are highly specific with respect to both the particular sugar "substrate" to be added and the acceptor molecule to which the substrate monosaccharide is transferred. The expression of glycosyltransferases, and hence, the composition of cell surface carbohydrates, is regulated in a species-specific, cell lineage-specific, and developmental stage-specific manner (Paulson and Colley, *J. Biol. Chem.*, 264: 17615–17618 (1989)).

Cell surface carbohydrates have been shown to play a key role in cell-cell recognition events mediated by protein-carbohydrate and carbohydrate-carbohydrate interactions (for example, Sharon and Lis, *Science,* 246: 227–234 (1989)). Cell surface carbohydrates can also function as receptor molecules for a large number of bacteria, bacterial toxins, viruses, and protozoa (see, Sharon and Lis, *Science,* 246: 227–234 (1989); Karlsson, *Ann. Rev. Biochem.,* 58: 309–350 (1989)).

Fucose residues play a key role in the histoblood group antigenic phenotype of eukaryotic cells, because they are a crucial component of the epitopes that define the A, B, O (H), and Lewis blood group antigen systems (see, for example, Clausen and Hakomori, *Vox Sang.,* 56: 1–20 (1989)). Fucosylated complex carbohydrates have also been identified as onco-fetal antigens and as adhesion molecules involved, for instance, in the early stages of an inflammatory response and in host-microbial interactions. In addition to *H. pylori,* *Candida albicans* (Tosh and Douglas, *Infect. Immun.* 60: 4734–4739 (1992)) and *Vibrio cholerae* (Sanchez and Jonson, *Acta Pathol. Microbiol. Immunol. Scand.,* 98: 353–357 (1990)) have been shown to express fucose-specific adhesion molecules. The syntheses of fucosylated sugars are regulated by the expression of specific fucosyltransferases (FTs). The genes coding for six different human FTs have been described. The first FT genes to be cloned were the human Lewis gene (Le) encoding human α1,3/4 FT (see, Kukowska-Latallo, et al., *Genes Dev.,* 4: 1288–1303 (1988)) and the human H gene encoding α1,2 FT (Larsen et al., *Proc. Natl. Acad. Sci. USA,* 87: 6674–6678 (1990)). In humans, the α1,3/4 FT can generate the sequence Galβ1-3/4(Fucα1-3/4)GlcNAc (FIG. 1) in complex carbohydrates on cellular membrane surfaces and is responsible for producing the stage-specific embryonic antigen 1 (SSEA-1) and the Lewis blood group antigens (Kukowska-Latallo et al., Genes Dev., 4: 1288–1303 (1990)). The α1,2 FT can add an L-fucose residue in an α1,2 position to a terminal galactose to generate the sequence Fucα1-2Galβ- in such surface carbohydrates and is responsible for generating the blood group H antigen, which is the molecule that structurally defines the blood group O phenotype (Clausen and Hakomori, *Vox Sang.,* 56: 1–20 (1989)).

The α1,2 FT cDNA sequence predicts a 365 amino acid protein product with the characteristics of a type II transmembrane glycoprotein (see, Larsen et al., *Proc. Natl. Acad. Sci. USA,* 87: 6674–6678 (1990)). The α1,3/4 FT is a 361 amino acid, type II transmembrane glycoprotein that was originally isolated using an expression cloning procedure based on the ability to produce SSEA-1 on the surface of transfected COS-1 cells (see, Kukowska-Latallo et al., *Genes Dev.,* 4: 1288–1303 (1990)). SSEA-1 is an oligosaccharide expressed during the murine preimplantation period and is thought to be involved in the process of compaction (Bird and Kimber, *Dev. Biol.,* 104: 449–460 (1984)).

DNA Sequences Encoding α1,2 FT and α1,3/4 FT

The cDNA sequences encoding the α1,2 FT and the α1,3/4 FT have previously been cloned and their sequences published (Larsen et al., *Proc. Natl. Acad. Sci. USA*, 87: 6674–6678 (1990) (α1,2 FT); Kukowska-Latallo et al., *Genes Dev.*, 4: 1288–1303 (1990) (α1,3/4 FT)). These are shown as Sequence ID No. 2 and 4, respectively.

Selection of Animals Useful for Construction of Transgenic Animals, and the Resulting Transgenic Animals Expressing the H1 and/or Lewis Antigen Animals that would be particularly useful as animal models are those which are easily bred, raised and readily manipulated genetically and biochemically. Such animals include the mouse, rat, gerbil, rabbit, hamster and guinea pig.

The following illustrates the criteria useful for selecting an animal species and strain used for creating an *H. pylori* infection model. General criteria include expression of potential acceptor molecules that could be used by human FTs to generate the H1 and/or Lewis antigen in the animal to be used; followed by expression of the H1 and/or Lewis antigen in the transgenic animal.

For example, the FVB/N strain of mice was chosen to generate this model as a result of several observations. First, the pit and enterocytic cell lineages of FVB/N mice contain potential acceptor molecules that could be used by human FTs to generate the H1 and/or Lewis antigens. Formation of the H antigen requires a carbohydrate core chain acceptor with a terminal galactose, preferably members of the lacto-series, and a soluble GDP-L-fucose substrate that is accessible to α1,2 FT for the transglycosylation reaction (see FIG. 1 and Larsen, et al., *Proc. Natl. Acad. Sci. USA*, 87: 6674–6678 (1990)). An in situ binding assay which uses fluorescent labeled galactose-specific lectins revealed the presence of such acceptors in the surface mucous, pit and enterocytic lineages of adult FVB/N mice (Falk, et al., *Am. J. Physiol.* (Gastroenterolo Liver Physiol., 266), G987–G1003, (1994)). For example, the lectin *Trichosantes kirilowii* (TKA) which binds to carbohydrate epitopes containing a terminal β-linked galactose, reacts with these FVB/N cell lineages in the stomach and intestine. Formation of the Lewis antigens requires a carbohydrate acceptor containing terminal Galβ1,3/4-GlcNAc or Fucα1,2 Galβ1,3/4-GlcNAc sequences with the GlcNAc serving as the site of attachment of L-fucose residues through the action of α1,3/4 FT (see FIG. 1 and Kukowska-Latallo, et al., *Genes Develop.*, 4: 1288–1303 (1990)). The in situ binding assay indicated that the surface mucous, pit and enterocytic lineages contain such acceptor molecules. Further evidence was shown by binding of these cells by both of the lectins *Erythrina christagalli* (ECA) and *Datura stramonium* (DSA), which recognize Galβ4GlcNAcβ- containing epitopes. These observations indicated that it should be possible to produce H1 and/or Lewis epitopes by expressing either one or both of the aforementioned human FTs in these FVB/N mouse gut epithelial cells.

The H1 and/or Lewis antigens can be readily detected in transgenic mice of this strain using lectins and the in situ binding assay. A normal adult FVB/N mouse that has not been genetically engineered to produce the human FTs, does not produce detectable levels of fucosylated glycoconjugates in their small intestinal enterocytes, a cell lineage that supports expression of reporter genes, such as fucosyltransferase with the Fabpl$^{-596\ to\ +21}$ promoter, as described below. Novel fucosylated carbohydrate epitopes could therefore be detected in these cells using fucose-specific lectins and monoclonal antibodies, as described below. In the FVB/N strain of mice, the fucose-specific lectins, *Ulex europaeus* agglutinin I (UEA-1), *Anguilla anguilla* agglutinin (AAA), and the *Lotus tetragonolobus* agglutinin only stain gastric surface mucous/pit cells and intestinal Paneth cells, M-cells, and subsets of goblet and enteroendocrine cells, but not enterocytes (Falk, et al., *Am. J. Physiol.* (Gastroenterol. Liver Physiol. 29, 266, G987–G1003), (1994)). Moreover, these antigens could be detected in transgenic FVB/N mice with other reagents which recognize fucose-containing glycoconjugates, such as commercially available monoclonal antibodies (MAbs) specific for blood group ABO(H) and Lewis antigens, or with FITC-labeled *H. pylori* and fixed sections of stomach, duodenum, jejunum, ileum and colon (Falk, et al., *Proc. Natl. Acad. Sci. USA*, 90: 2035–2039 (1993)).

Design of α1,2 FT and α1,3/4 FT Transgenes a. Tissue-specific Promoters

To increase the accuracy and reliability of an animal model for *H. pylori* adhesion and infection, it is desirable that proper genetic controls direct expression of cell surface receptors for bacterial adhesins in the relevant cell lineages of the gut epithelium, such as in surface mucous and pit cells. A preferred example of a suitable promoter is the promoter sequence Fabpl$^{-596\ to\ +21}$ contained within nucleotides (nt) −596 to +21 of the rat liver fatty acid binding protein gene (Fabpl) (nucleotides 1 to 617 of Sequence ID No. 5) which can direct foreign gene expression to the pit cell lineage of the mouse gastric epithelium, to proliferating and nonproliferating cells in intestinal crypts, as well as to the four principal differentiated cell lineages distributed along the crypt-to-villus axis of the small intestine (Roth et al., *Am. J. Physiol.* (Gastrointest. Liver Physiol., 26), 263: G186–G197 (1992); Trahair et al., *J. Cell Biol.*, 109: 3231–3242 (1989); Simon et al., *J. Biol. Chem.*, 268: 18345–18358 (1993), incorporated herein by reference).

The Fabpl promoter sequences or other such tissue-specific promoter sequences are inserted upstream of the coding sequences for α1,2 FT and/or α1,3/4 FT to direct synthesis of H and Lewis blood group antigens in the gut epithelium of animals containing the recombinant DNAs as transgenes.

b. Expression Enhancers

Other nucleic acid sequences can also be incorporated into the design of the α1,2 FT and α1,3/4 FT transgenes. For example, recombinant DNA molecules can be made in which a cDNA encoding a human FT is inserted downstream of the Fabpl$^{-596\ to\ +21}$ promoter sequence and into exon 1 of a human growth hormone gene (hGH, Seeburg, *DNA*, 1: 239–249 (1982)) sequence consisting of nucleotides +3 to +2150 of the hGH gene (nucleotides 620 to 2771 of Sequence ID No. 5). No human growth hormone should be produced from such recombinant DNAs because the translational initiator Met codon and the first translational stop codon are from the fucosyltransferase DNA, and there is no ribosomal re-entry sequence to re-initiate translation at the downstream initiator Met codon of the hGH gene sequence. The hGH gene sequence insures efficient splicing of the primary transcription product of the transgene, improves the stability of the cytoplasmic fucosyltransferase mRNA (Sandgren, et al., *Cell*, 61: 1121–1135 (1991)) and allows expression of the transgene to be monitored either by immunocytochemical methods using an antibody directed against the fucosyltransferase or by in situ hybridization using a digoxigenin-labeled hGH oligonucleotide (Simon, et al., *J. Biol. Chem.*, 268: 18345–18358 (1993)).

Production of Transgenic Mice

Transgenic animals can be generated by standard methods in which a genetic construct is introduced by pronuclear injection into a fertilized egg. The most common methods of such direct introduction of gene sequences are microinjection of embryos and injection of embryonic stem cells into blastocysts. The procedures for manipulation of the rodent embryo and for microinjection of DNA are described in detail in Hogan et al., *Manipulating the mouse embryo*, (Cold Spring Harbor Laboratory, Cold Spring Harbor, N.Y., 1986), the teachings of which are incorporated herein. Embryonic stem (ES) cells can be manipulated using the method of Gossler, et al., "Transgenesis by means of blastocyst-derived embryonic stem cell lines" *Proc. Natl. Acad. Sci. USA*, 83: 9065–9069 (1986), the teachings of which are incorporated herein. The use of nucleotides 1 to 617 (Sequence ID No. 5) of rat Fabpl (Fabpl$^{-596\ to\ +21}$) in gene expression in embryonic stem cell components of chimeric transgenic mice are described in Hermiston, et al. (*Proc. Natl. Acad. Sci. USA*, 90: 8871–8875 (1993)) which also describes methods for distinguishing ES cell components of chimeric gut epithelium from normal host blastocyst components by means of their different patterns of glycoconjugate expression.

Typically, when microinjected embryos are to be used to produce transgenic mice, female mice six weeks of age are induced to superovulate, for example, with a 5 IU injection (0.1 cc, intraperitoneally (ip)) of pregnant mare serum gonadotropin (PMSG, Sigma, St. Louis, Mo.), followed 48 hours later by a 5 IU injection (0.1 cc, ip) of human chorionic gonadotropin (hCG, Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline (DPBS) with 0.5% bovine serum albumin (BSA, Sigma). Surrounding cumulus cells are removed with hyaluronidase (for example, 1 mg/mL). Pronuclear embryos are then washed and placed in a buffer such as Earle's balanced salt solution containing 0.5% BSA (EBSS) in a 37.5° C. incubator with a humidified atmosphere at 5% $CO_2$, 95% air until the time of microinjection.

Purified linear DNA molecules including an FT transgene construct are purified and diluted to 5 ng/mL in Buffer A (10 mM Tris/0.2 mM EDTA, pH 7.4). The diluted DNA is then filter sterilized and injected into the male pronucleus of newly fertilized mouse oocytes using standard microinjection methods (see, Hogan et al., *Manipulating the mouse embryo*, pp. 157–173 (Cold Spring Harbor Laboratory, Cold Spring Harbor, N.Y., 1986)).

Once the embryos are injected, the live embryos are transferred into foster mothers. Foster mothers are produced from randomly cycling adult female mice paired with vasectomized males. Swiss Webster or other comparable strains can be used for this purpose. Recipient females are mated at the same time as donor females. At the time of embryo transfer, the recipient females are anesthetized with an intraperitoneal injection of, for example, 0.015 mL of 2.5% avertin per gram of body weight. The oviducts are exposed by a single midline dorsal incision. An incision is made through the body wall directly over the oviduct. The ovarian bursa is torn, for example, with watchmakers forceps. Embryos to be transferred are placed in DPBS or other comparable buffer and withdrawn into the tip of a transfer pipet (about 10–12 embryos). The pipet tip is inserted into the infundibulum and the embryos transferred. After the transfer, the incision is closed with sutures, and the foster mothers are housed, one or two per cage.

Creating Bi-transgenic Mice That Co-express α1,2 and α1,3/4 FTs in Gut Epithelial Cell Lineages In cells that contain fucosylated glycocojugates (for example, members of the surface mucous and pit lineages of the FVB/N mouse stomach), expression of a single additional human FT could be sufficient for *H. pylori*. However, in gut epithelial cells lacking endogenous fucosylated glycoconjugates, it is necessary to express both α1,2 and α1,3/4 FTs to produce the Lewis b receptor. A relatively easy way to obtain transgenic animals expressing two transgenes is to mate two animals, each of which expresses one of the transgenes (see, for example, Kim et al., *J. Cell Biol.*, 123: 877–893 (1993); Khillan et al., *Nucleic Acids Res.*, 16: 1423–1430 (1988)). For example, a male or female mouse containing a transgene consisting of rat Fabpl$^{-596\ to\ +21}$ linked to α1,2 FT-hGH can be mated to a mouse containing a transgene consisting of rat Fabpl$^{-596\ to\ +21}$ linked to α1,3/4 FT-hGH, to produce progeny containing and expressing both transgenes.

Screening for α1,2 FT and α1,3/4 FT Transgene Expression in Transgenic Animals

The expression of α1,2 FT and α1,3/4 FT in transgenic animals can be determined by a variety of methods.

1. Screening with nucleic acid probes

Nucleic acid probes can be used to detect the presence of the transgenes in an animal genome. For example, tail samples (0.5–1 cm) can be removed from three week old mice, and the DNA prepared and analyzed by both Southern blotting (using $^{22}P$ labeled FT DNA as probes) and PCR (using Fabpl, hGH and/or FT oligonucleotides) to detect transgenic founder ($F_0$) animals and their progeny ($F_1$ and $F_2$). In addition, cDNA sequences used to construct the FT transgenes can be used in RNA blot hybridization, RNAse protection, and/or reverse transcriptase PCR assays, to detect FT-hGH mRNA transcripts in the cells of various tissues, especially the cells of gut epithelial tissue.

2. Screening for binding to receptors

Alternatively, new carbohydrate antigen receptors for *H. pylori* generated on the surface of cells of gut epithelium by the expression of functional α1,2 FT and/or α1,3/4 FT can be detected using one or more appropriate lectins or monoclonal antibodies (MAbs), which bind specifically to the H antigen or to a particular Lewis antigen.

a. Lectins

Lectins are proteins which bind specific carbohydrate structures. Such proteins can be used to detect the presence of carbohydrate epitopes in the gut epithelium of a host animal (Falk, et al., *Am. J. Physiol.* (Gastroenterol. Hepatol., 29), 266, G987–G1003, (1994)). Lectins that are useful for specifically detecting the presence of fucosylated glycoconjugates, such as the H antigen and Lewis antigens, on the surfaces of gut epithelial cells include *Ulex europaeus* agglutinin I (UEA-I), *Anguilla anguilla* agglutinin (AAA), and *Lotus tetragonolobus* agglutinin. (Falk, et al., *Am. J. Physiol.* (Gastroenterol. Hepatol., 29,) 266, G987–G1003) (1994)).

b. Monoclonal antibodies

Monoclonal antibodies (MAbs) which bind to specific carbohydrate structures, such as H or Lewis antigens are commercially available (for example, DAKO, Carpinteria, Calif.; Immucor, Inc., Norcross, Ga.; Signet Lab. Inc., Dedham, Mass.). As with lectins, MAbs directed against specific carbohydrates can be used to detect the presence of carbohydrate structures on the gut epithelial cells of transgenic and non-transgenic animals. Since most MAbs are produced in mice, they can be directly conjugated with a fluorochrome, such as fluorescein isothiocyanate, tetramethyl-rhodamine isothiocyanate or Cy3™, or with digoxigenin groups (see Section c., below) allowing detection with, for example, Fab fragments of sheep anti-digoxigenin (Boehringer-Mannheim, Indianapolis, Ind.) conjugated with fluorescent or enzyme (alkaline phosphatase, horseradish peroxidase) tags.

c. *H. pylori* or its membrane fragments

As an alternative to using either lectins or MAbs, *H. pylori* cells can be labelled, for example, with fluorescein isothiocyanate or digoxigenin-3-O-succinyl-ε-aminocaproic acid N-hydroxysuccinimide ester (DIG-NHS, Boehringer Mannheim, Indianapolis, Ind.), and used as a diagnostic reagent to bind and detect the newly synthesized surface *H. pylori* receptors on the surface of gut epithelial cells of transgenic animals (see, Falk et al., *Proc. Natl. Acad. Sci. USA*, 90: 2035–2039 (1993); Borén et al., *Science*, 262: 1892–1895 (1993)).

Use of α1,2 FT and α1,3/4 FT Transgenic Animals

A transgenic animal expressing either or both α1,2 FT and α1,3/4 FT generates the H and/or $Le^b$ cell surface carbohydrate antigens and therefore is a powerful model for studying the effects of *H. pylori* on gut epithelial biology. Such animals constitute the first genetically well-defined and manipulable animal model of *H. pylori* adhesion and infection. The animal model can be used to systematically screen for compounds that block binding of *H. pylori* to the gut epithelium and/or ameliorate the effects of *H. pylori* binding on the pathogenesis of acid peptide disease, for example, gastritis, stomach ulcers, duodenal ulcers, and gut neoplasia, such as stomach adenocarcinoma.

1. Establishment of Infection with *H. pylori*

*H. pylori* bacteria can be orally administered to establish an infection in the gut epithelium of transgenic animals which express the H antigen and/or $Le^b$ antigens. The establishment of the *H. pylori* infection can be confirmed by examining tissue samples for bacteria and/or signs of inflammation, ulceration or carcinoma. Once the bacterial infection has been established, a compound or a series of compounds can then be administered to the infected animal at various times and in various dosages, depending on the particular goals of the screen. In a variation of this procedure, it may be desirable to administer the bacteria with a compound to determine whether, relative to control animals, the compound can effectively prevent in vivo the initial bacterial adhesion and/or the subsequent establishment of infection or pathogenesis.

2. Screening for compounds blocking infection

The efficacy of the compound or compounds can be assessed by examining at selected times the cells of the gut epithelial tissue of the infected animals for the presence or loss of adherent *H. pylori* bacteria and/or the development, inhibition, or amelioration of ulcer or tumor formation relative to appropriate control mice, for example, untreated *H. pylori*-infected animals.

This is particularly useful in the testing of vaccines against the bacteria, which are administered to the animal approximately ten days prior to exposure to the bacteria, and thereafter as required to produce immunity against infection or development of a disorder associated with infection.

Since the described transgenic animals express the receptors which bind *H. pylori* in human gut epithelium, they offer the additional benefit of allowing the efficacy of various drugs or compounds to be readily assessed based on different modes of administration and compound formation. In addition to using the transgenic animals to screen for therapeutic compounds, these animals can also be used to screen for conditions or stimuli which effect a block in or ameliorate *H. pylori* adhesion, infection and/or associated gut diseases. Such stimuli or conditions include environmental or dietary changes, changing the gastro-intestinal pH, or combinations of various stimuli or conditions which result in stress on the animal or on *H. pylori* bacteria in the gut. *H. pylori* can be administered to the described transgenic animals, and the animals then exposed to a selected stimulus or condition, or a combination of stimuli or conditions, to be tested. The gut epithelial tissue of exposed transgenic animals is then examined periodically for a change in the number of adherent *H. pylori* bacterial and/or the disease state of the epithelial tissue relative to non-exposed control transgenic animals.

Another type of condition that can be tested for its effect on *H. pylori* adhesion, infection, and/or associated gut disease in the transgenic animals described herein is the induction of an inflammatory response, for example by administering a chemical agent such as dextran sulfate, at various times prior to, during, or after administration of *H. pylori* to the transgenic animal. The inflammatory agent can be administered orally or by any other mode that results in a gastrointestinal inflammatory response. The severity of the inflammatory response can be controlled by varying the dose and the duration of treatment with the chemical agent.

3. Other Uses of Transgenic Animals Expressing *H. pylori* Receptor Molecules.

Transgenic animals expressing *H. pylori* receptor molecules can also be used as a source of epithelial cells which can be cultured and infected in vitro with *H. pylori*. For example, conditionally immortalized gut epithelial cells can be produced from transgenic mice containing $Fabpl^{-596\ to\ +21}$ linked to a gene coding for a temperature sensitive Simian virus 40 T antigen. (TAg) (Jat and Sharp, Mol. Cell Biol., 9, 1672–1681 (1988)). The temperature sensitive TAg is inactive at 37°–40° C. but is active at 33° C. allowing cells that express the protein to continuously proliferate at the latter temperature. Cells carrying the TAg transgene can be harvested from transgenic animals and grown in primary cell culture at 33° C. to establish conditionally immortalized lines. The differentiation programs of cloned, established cell lines can then be induced by switching the incubation temperature to 39° C. If such animals are crossed to animals containing a single FT transgene or to an α1,2 FT/α1,3/4 FT bi-transgenic mice creating TAg/FT expressing bi- or tri-transgenic animals that could be a source of H1 and/or $Le^b$ producing gut epithelial culture cell lines. Such cultured cells can be used for rapid in vitro screening protocols for compounds that block *H. pylori* adhesion and infection. *H. pylori* adhesion to such cultured cells can readily be determined in vitro, using manual, semi-automated or automated methods as, for example, through the use of commercially available fluorescently labeled antibodies to *H. pylori* (Harlan Bioproducts for Science, Indianapolis, Ind.). Compounds that are initially identified as inhibitors of *H. pylori* adhesion or infection in such an in vitro system can then be further screened and studied for their in vivo efficacy against *H. pylori* using a transgenic animal as described above and below.

Germ-free (see, for example, Granholm, et al., *Cytokine*, 4, 545–550 (1992)) transgenic animals can be generated by embryo transfer into gnotobiotic females raised in isolator cages. These germ-free transgenic animals can be monocontaminated with laboratory strains of *H. pylori* or various clinical isolates to directly examine the pathogenesis of *H. pylori* infection and the efficacy of drugs in modifying the course or extent, of infection and associated gastrointestinal pathology in the absence of a normal microflora.

Gastric or intestinal isografts can be prepared from embryonic day 15 transgenic animals and implanted into the subcutaneous tissues of normal young adult syngeneic hosts, for example, by using previously established methods (Rubin, et al., *J. Biol. Chem.*, 267: 15122–15133 (1992); Rubin, et al., *Am. J. Physiol.* (Gastroenterol. Liver Physiol., 30), 267, G27–G39, (1994)). These isografts support differentiation of the various gut epithelial cell lineages in the absence of a microflora or pancreatic and biliary secretions. They can be infected with *H. pylori* by introducing the organism through a cutaneous injection with a sterilized needle and syringe. The effects of the organism in isografts can be assessed in the presence or absence of compounds that may block binding of the bacteria to cellular receptors or alter the course of infection.

The colonization of the intact gut from germ-free and monocontaminated mice, as well as isografts, can be assessed by an in situ binding assay (Falk, et al., *Am. J. Physiol.* (Gastroenterol. Liver Physiol. 29), 266, G987–G1003), (1994); Falk, et al., *Proc. Natl. Acad. Sci. USA* 90,2035–2039 (1993)). Furthermore, the degree of mucosal inflammatory response and metaplasia/dysplasia will be evaluated using standard histochemical stains, such as hematoxylin/eosin, periodic acid Schiff (PAS), Alcian blue, and high iron diamine (Baracchini, et al., Histochem. J., 23, 1–9 (1991)). The presence of bacteria on the epithelial cell surface can be detected using standard histochemical methods such as special Giemsa and Warthin-Starry silver stain (Madan, et al., *Am. J. Clin. Pathol.*, 90: 450–453 (1988)).

Additional guidance can be obtained by the following non-limiting examples.

EXAMPLE 1

$\alpha 1,2$ FT and $\alpha 1,3/4$ FT gene sequences

Figure 2:
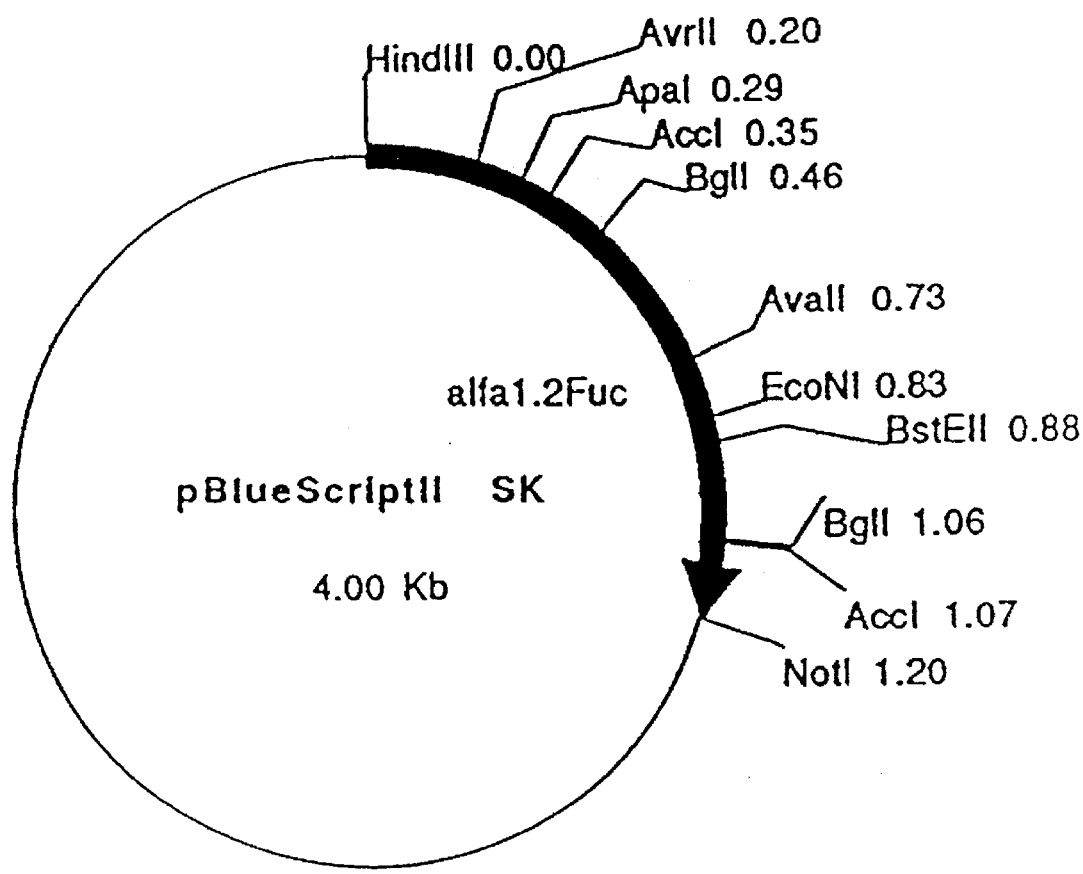
FIG. 2 is a diagram of the recombinant pBLUESCRIPT™ II (Stratagene, La Jolla, Calif.) SK-α1.2 FT vector showing relative positions of selected restriction endonuclease sites.
Figure 3:
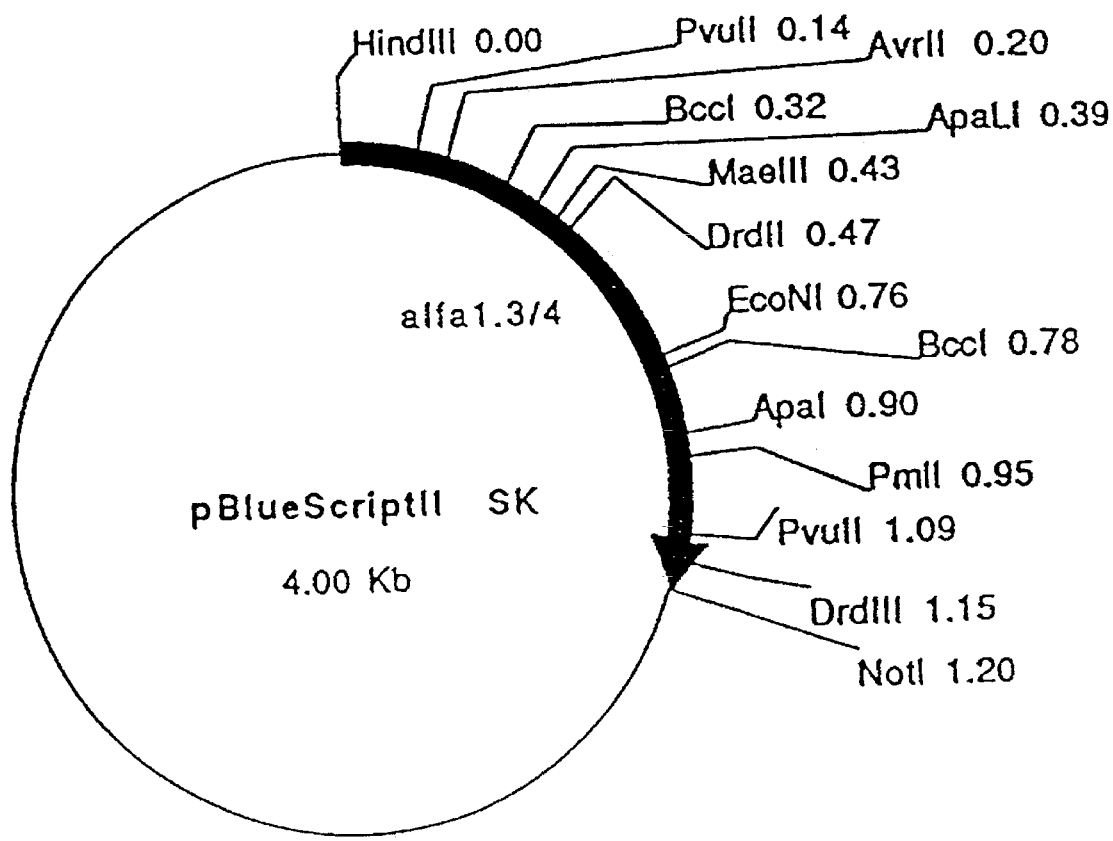
FIG. 3 is a diagram of the recombinant pBLUESCRIPT™ II (Stratagene, La Jolla, Calif.) SK-α1.3/4 FT vector showing relative positions of selected restriction endonuclease sites.

Cloned cDNAs for $\alpha 1,2$ FT and $\alpha 1,3/4$ FT were provided in pCDM8 (see, Ausubel, F. M. et al., In *Current Protocols in Molecular Biology, Volume 2*, pp. 6.13.1–16.13.7 (John Wiley & Sons, New York, 1991)) by Dr. Jan Holgersson (Department of Molecular Biology, Massachusetts General Hospital, Boston, Mass.). These sequences were recovered using polymerase chain reaction (PCR) primers based on the published sequences (Kukowska-Latallo, et al., *Genes Develop.*, 4: 1288–1303 (1990) for $\alpha 1,3/4$ FT DNA sequence; Larsen et al., *Proc. Natl. Acad. Sci. USA*, 87: 6674–6678 (1990) for $\alpha 1,2$ FT DNA sequence; incorporated herein by reference) and human placental DNA as the template DNA. The FT gene sequences were engineered to contain a 5' HindIII site, a Kozak consensus sequence followed by the open reading frame (ORF) for each FT protein of approximately 1.1 kilobases (kb), and a 3' NotI site. The positions of the HindIII and NotI sites are evident in FIGS. 2 and 3. This allowed insertions of the FT sequences into the corresponding HindIII and NotI sites of pCDM8. The PCR cloned $\alpha 1,2$ FT and $\alpha 1,3/4$ FT genes have been expressed in COS1 cells and performed the expected transglycosylation reactions.

The cDNA sequences encoding each FT were excised from the recombinant pCDM8 vectors by digestion with HindIII and NotI, and the 1.1 kb HindIII-NotI fragments containing the cloned FT-coding sequences were gel purified using GENECLEAN™(BIO 101 Inc., La Jolla, Calif.). The purified 1.1 kb fragments were then cloned into the HindIII/NotI polylinker sites of pBLUESCRIPT™IISK vectors (Stratagene, La Jolla, Calif.) for easier manipulation. Restriction analysis confirmed that the desired recombinant pBLUESCRIPT™ vectors were made (see FIGS. 2 and 3).

The 1.1 kb fragments containing sequences encoding either the $\alpha 1,2$ FT or the $\alpha 1,3/4$ FT were released from the recombinant pBLUESCRIPT™ vectors by digestion with HindIII and NotI, and the fragments gel purified, as described above, for use in constructing $\alpha 1,2$ FT and $\alpha 1,3/4$ FT transgenes.

EXAMPLE 2

Construction of Transgenes

Figure 4:
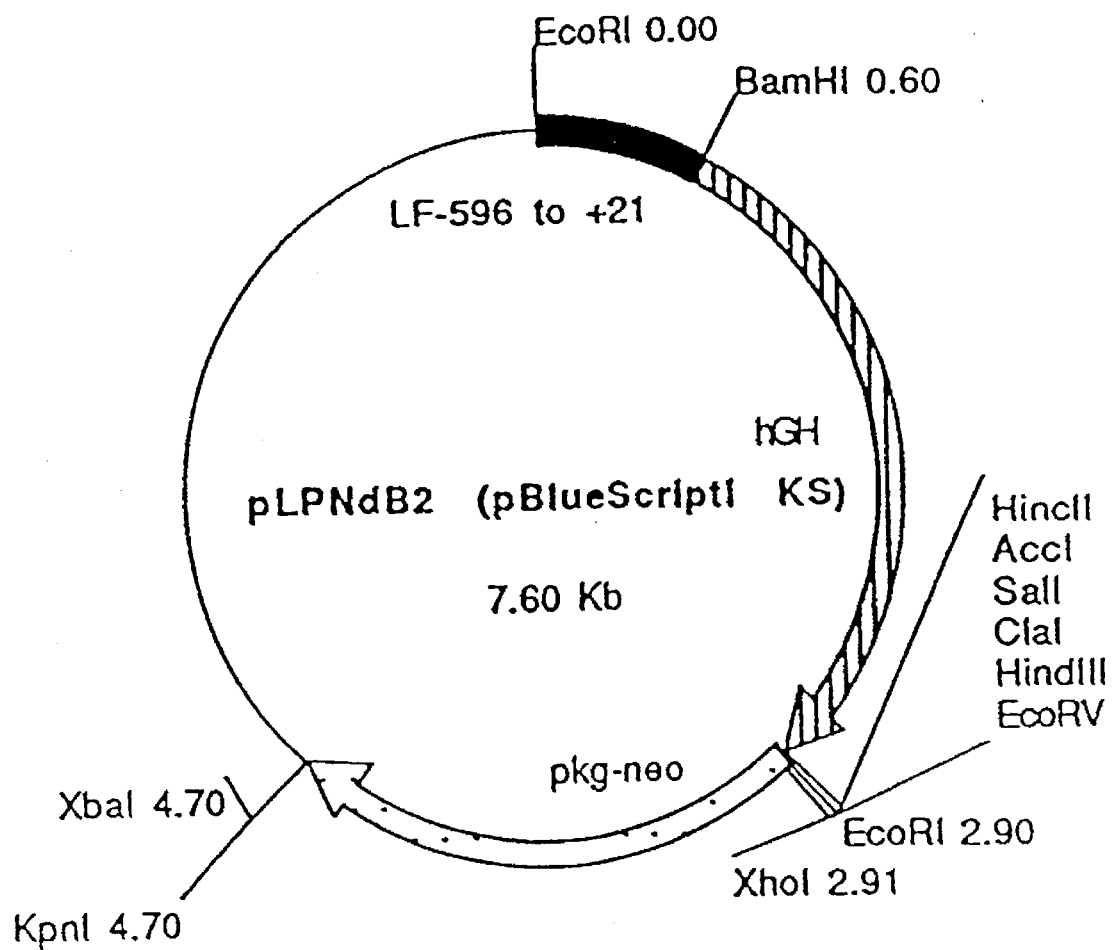
FIG. 4 is a diagram of pLPNΔB2 showing relative position of nucleotides (nt)–596 to +21 of the rat Fabpl gene which corresponds to nucleotides 1 to 617 of Sequence ID No. 5, linked to nucleotide +3 to +2150 of the human growth hormone (hGH) gene which corresponds to nucleotides 620 to 2771 of Sequence ID No. 5, and pgK-neo. The pgK-neo marker is a neomycin resistance selection cassette under the control of the phosphoglycerate kinase promoter, but is not a part of the 4 kilobase (kb) gene construct that was injected into embryos described in Example 3. The relative positions of selected restriction endonuclease sites are also shown.
Figure 5:
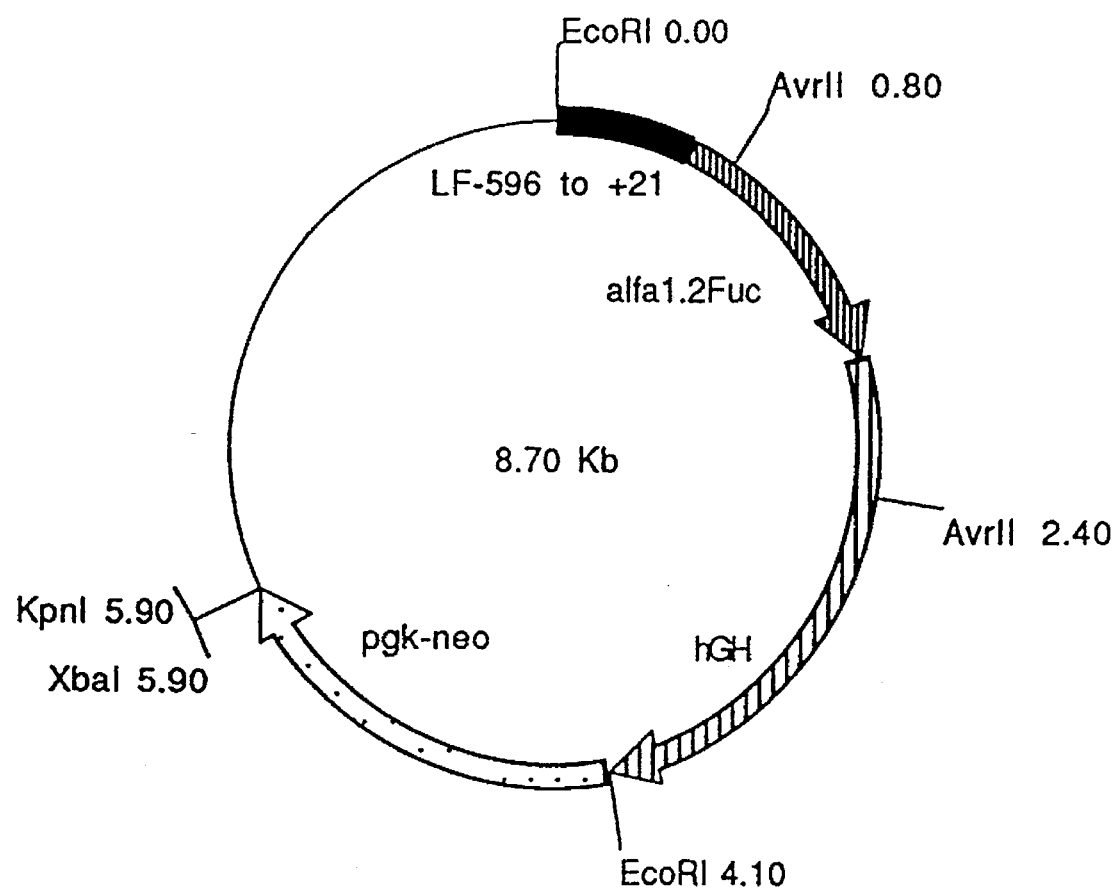
FIG. 5 is a diagram of plasmid LF-α1,2 FT showing relative positions of nucleotides −596 to +21 of the rat Fabpl gene (nucleotide 1 to 617 of Sequence ID No. 5), nucleotides +3 to +2150 of the hGH gene (nucleotides 620 to 2771 of Sequence ID No. 5), and the 1113 nucleotide α1,2 FT sequence including the 1096 nucleotide α1,2 FT coding region, (Larsen, et al., *Proc. Natl. Acad. Sci. USA,* 87: 6674–6678 (1990)) (nucleotides 104 to 1201 of Sequence ID No. 2), the 5' (upstream of the transcriptional start site) HindIII site and Kozak concensus sequence (AGCTTGCCACC, Sequence ID No. 11) not in the published sequence, and the 3' (downstream of the translational stop codon) NotI (GCGGCCGC) site. The relative positions of selected restriction endonuclease sites are also shown.
Figure 6:
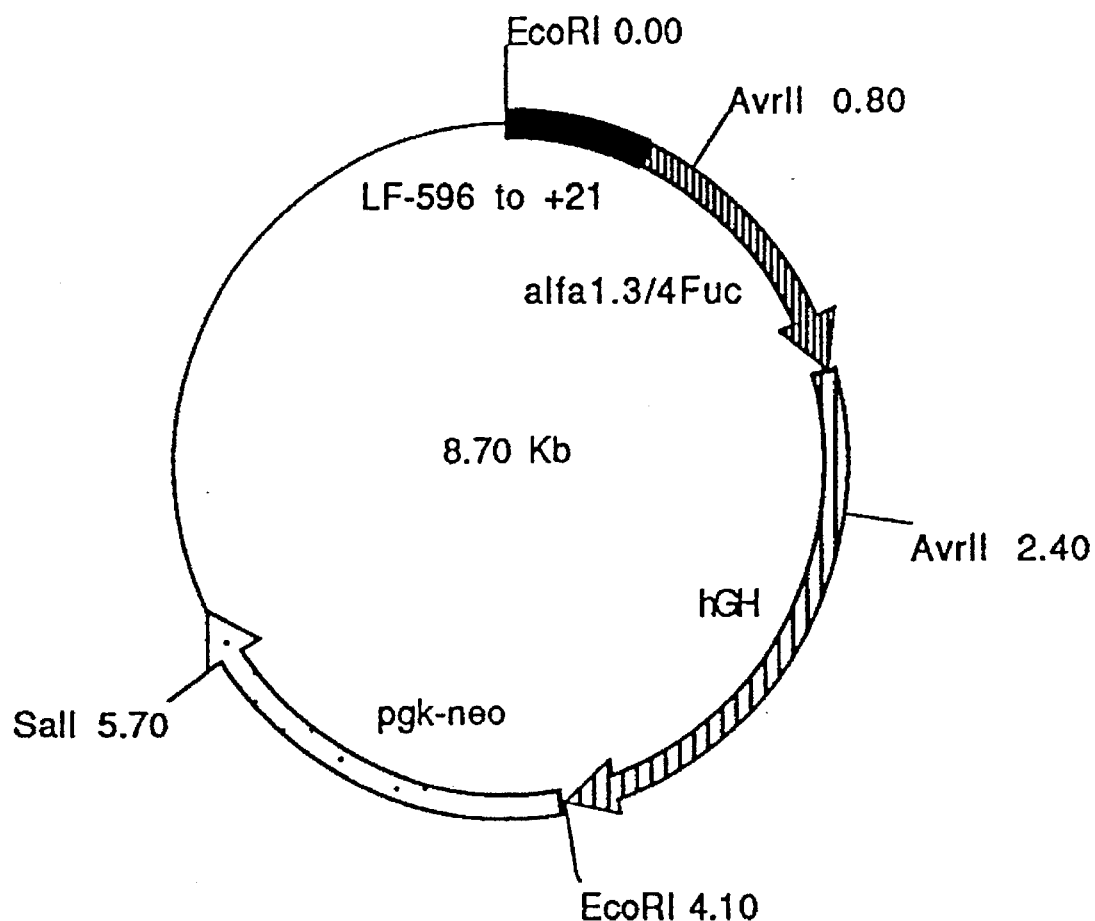
FIG. 6 is a diagram of plasmid LF-α1.3/4 FT showing relative positions of nucleotides −596 to +21 (nucleotides 1 to 617 of Sequence ID No. 5) of the rat Fabpl gene, nucleotides +3 to +2150 (nucleotides 620 to 2771 of Sequence ID No. 5) of the hGH gene, and the 1103 nucleotide α1,3/4 FT sequence including the 1086 nucleotide coding region (nucleotides 73 to 1158 of Sequence ID No. 4), the 5' (upstream of the start site of transcription) HindIII site and Kozak consensus sequence and the 3' NotI site (analogous to FIG. 5).

The 1.1 kb FT HindIII/NotI fragments from the recombinant pBLUESCRIPT™ vectors were isolated as described above and blunt-ended with Klenow fragment. The blunt-ended fragments were each gel purified and inserted into the unique BamHI site of vector pLPNΔB2 which, as shown in FIG. 4, is a derivative of pBLUESCRIPT™I KS and contains nucleotides −596 to +21 of the rat Fabpl promoter sequence (nucleotides 1 to 617 of Sequence ID No. 5), the gene sequence encoding the human growth hormone (hGH) (nucleotides 620 to 2771 of Sequence ID No. 5) and the pgk-neo selection cassette (FIG. 4). Each fragment was inserted into the BamHI site of the pLPNΔB2 vector, after the opened BamHI site had been blunt-ended with Klenow fragment, thereby forming recombinant plasmids with each fragment at the proper position between the Fabpl$^{-596\ to\ +21}$ promoter sequence and the hGH exon 1 sequence. The recombinant plasmids were then transformed into *E. coli* DH5α cells. Transformants were screened for recombinant plasmids containing inserts in the proper orientation by digesting plasmid DNAs with AvrII, which generates a 1.6 kb fragment in the case of a correctly oriented insert. Diagrams of recombinant plasmid Fabpl$^{-596\ to\ +21}$/$\alpha 1,2$ FT/hGH containing the $\alpha 1,2$ FT sequence in the proper orientation and of recombinant plasmid Fabpl$^{-596\ to\ +21}$/$\alpha 1,3/4$ FT/hGH containing the $\alpha 1,3/4$ FT sequence in the proper orientation are shown in FIGS. 5 and 6, respectively.

The integrity of the junctions between the FT fragments and pLPNΔB2 vector sequences was assessed by sequencing 400 base pairs across the Fabpl$^{-596\ to\ +21}$/FT and FT/hGH junctions, respectively. The sequences at the 5' and 3' junctions were as expected.

EXAMPLE 3

Microinjection of Embryos

The DNA constructs, Fabpl$^{-596\ to\ +21}$/$\alpha 1,2$ FT/hGH and Fabpl$^{-596\ to\ +21}$$\alpha 1,3/4$ FT/hGH, were released from vector DNAs using EcoRI. Four kb fragments containing the -Fabpl$^{-596\ to\ +21}$/$\alpha 1,2$ FT/hGH or Fabpl$^{-596\ to\ +21}$/$\alpha 1,3/4$ FT/hGH constructs (see FIGS. 5 and 6) were purified by cleavage of the remaining 4.7 kb vector DNA sequences using Kpnl (for isolating the $\alpha 1,2$ FT encoding DNA construct) and ScaI (for isolating the $\alpha 1,3/4$ FT encoding DNA construct), followed by agarose (1%) gel electrophoresis. Each 4 kb fragment was cut out of the gel and gel purified using the GENECLEAN System™ (BIO 101, Inc., LaJolla, Calif.). The purity of the Fabpl$^{596\ to\ +21}$/$\alpha 1,2$ FT/hGH and Fabpl$^{596\ to\ +21}$/$\alpha 1,3/4$ FT/hGH constructs was confirmed by agarose gel electrophoresis. The concentration of each purified fragment was determined by fluorimetry.

For microinjection, the DNA fragments were diluted to 5 ng DNA/ml in Buffer A(10 mM Tris/0.2 mM EDTA, pH 7.4), and filter sterilized using a 0.22 μm ULTRA-FREE™-MC filter unit (Millipore Corp., Bedford, Mass.). The purified DNA was then injected into the male pronucleus of newly fertilized FVB/N mouse oocytes using standard microinjection methods (see, for example, Hogan et al., *Manipulating the mouse embryo*, pp. 157–173 (Cold Spring Harbor Laboratory, Cold Spring Harbor, N.Y., 1986)).

EXAMPLE 4

Screening for Transgenic Founder Mice Expressing $\alpha 1,2$ FT and $\alpha 1,3/4$ FT The DNA from tail samples of putative transgenic mice has been isolated and probed with $\alpha 1,2$ FT and $\alpha 1,3/4$ FT gene sequences to determine by standard DNA blotting methods whether a particular FT gene has been incorporated into the genome of the mice. Alternatively, the Fabpl$^{-596}$ $^{to}$ $^{+21}$/FT/hGH transgene constructs can be detected in tail DNA by PCR using primers (5'-AGCTG-GCCTTTGACACCTACCAGG-3' (nucleotides 1 to 24 of Sequence ID No. 6) (sense strand of exon 1) and 5'-TCT-GTTGTGTTTCCTCCCTGTTGG-3' (Sequence ID No. 7) (antisense strand exon 3)) derived from hGH sequences corresponding to intron 2 (a 352 bp fragment), or portions of the coding regions of the human FT DNAs. The PCR reactions for detecting human FT DNAs in transgenic animals employ 5'-CGACAATCACTGACCTATGGCC-3' of Fabpl promoter sequence corresponding to nucleotides 520 to 541 Sequence ID No. 5 (sense strand) and 5'-CGGCG-GTCTGGACACAGGATCG-3' (nucleotides 219 to 240 of Sequence ID No. 8), corresponding to nucleotides +116 to +137 of the anti-sense strand of the human α1,2 FT DNA ORF or open reading frame (a 230 bp fragment), or 5'-GGC-CAGGTAGAACTTGTACCGGG-3' (Sequence ID No. 9), corresponding to nucleotides +715 to +737 of the anti-sense strand of human α1,3/4 FT DNA ORF (an 830 bp fragment). Lines of transgenic animals have been established by crossing founder mice to normal (non-transgenic) FVB/N littermates.

Expression of α1,2 FT and α1,3/4 FT in transgenic mice is determined using lectins or MAbs which bind to the specific carbohydrate structures which are predicted to be generated by expression of the FTs. As noted above, a variety of lectins have been identified which can be useful for detecting the presence of various carbohydrate structures found on normal mouse gut epithelial cells (see Falk et al., *Am. J. Physiol.* (Gastrointest. Liver Physiol. 29), 266, G987–G1003), (1994)). Lectins which are specific for fucosylated glycoconjugates include *Ulex europaeus* agglutinin I (UEA-1), *Anguilla anguilla* agglutinin (AAA), and *Lotus tetragonolobus* agglutinin.

As an alternative to using either lectins or MAbs, *H. pylori*, itself, is labeled, for example, with fluorescein isothiocyanate or digoxigenin-3-O-succinyl-ε-aminocaproic acid N-hydroxysuccinimide ester (Dig-NHS, Boehringer Mannheim), and used to detect the newly synthesized surface carbohydrate receptors on the surface of cells of tissue samples of the transgenic mice as described by Falk et al., *Proc. Natl. Acad. Sci. USA*, 90: 2035–2039 (1993) and Borén et al., *Science*, 262: 1892–1895 (1993)).

Modifications and variations of the transgenic animal models for screening of antiviral compounds and vaccines, and method of making, will be obvious to those skilled in the art. Such modifications and variations are intended to come within the scope of the appended claims.

We claim:

1. A transgenic mouse expressing in its gut epithelial cells, under control of a gut epithelial cell specific promoter, an enzyme selected from the group consisting of human GDP-L-fucose: β-D-galactoside 2-α-L fucosyltransferase and human GDP-L-fucose: β-D-N-acetylglucosamide 3/4-α-L-fucosyltransferase, wherein Helicobacter pylori adhere to the gut epithelial cells.

2. The transgenic mouse of claim 1 wherein the mouse is gnotobiotic.

3. Gut epithelial cells cultured in vitro from the transgenic mouse of claim 1 or 2, wherein the cells express the enzyme and bind Helicobacter pylori.

4. A method of making a transgenic mouse model or an in vitro mouse gut epithelial cell model for Helicobacter pylori adhesion to gut epithelial cells comprising:

introducing into a living mouse embryo DNA molecules comprising the coding sequence for a functional human GDP-L-fucose: β-D-galactoside 2-α-L-fucosyltransferase or human GDP-L-fucose: β-D-N-acetylglucosamide 3/4-α-L-fucosyltransferase, operably linked to a gut epithelial cell specific promoter;

transferring the embryo to a foster mother; and assaying the resultant born mouse for the adhesion of H. pylori to gut epithelial cells.

5. A method to screen a compound for the ability to inhibit Helicobacter pylori adhesion to gut epithelial cells comprising:

administering Helicobacter pylori bacteria to a transgenic mouse of claim 1, or cultured gut epithelial cells derived from the transgenic mouse, wherein the Helicobacter pylori bacteria adhere to gut epithelial cells in the transgenic mouse, or the cultured gut epithelial cells;

assaying the gut epithelial cells of the transgenic mouse, or the cultured gut epithelial cells, to determine the number of adherent Helicobacter pylori bacteria on the surface of the cells;

administering the compound to be screened to the mouse or cells; and assaying the gut epithelial cells to determine if the compound decreased the number of adherent Helicobacter pylori bacteria.

6. The method of screening of claim 5, wherein the Helicobacter pylori bacteria are administered first to the transgenic mouse, or the cultured cells derived from the transgenic mouse; the Helicobacter pylori are allowed to adhere; and then the compound to be tested is administered to the infected transgenic mouse, or the cultured cells derived from the transgenic mouse.

7. The method of screening of claim 5, further comprising comparing the decrease in number of bacteria adherent to the gut epithelial cells of the transgenic mouse to the decrease in number of bacteria adherent to the gut epithelial cells of a transgenic mouse not exposed to the compound to be screened.

8. The method of screening of claim 7 further comprising exposing the mouse to a stimulus or condition selected from the group consisting of dietary changes, gastro-intestinal pH changes, changes in ambient temperature, changes in body temperature, and chemical induction of an inflammatory response.

9. The method of claim 7 wherein the mouse is vaccinated with a vaccine against Helicobacter pylori about 10 days prior to administration of the bacteria to the mouse.

* * * * *